United States Patent
Brady et al.

(10) Patent No.: US 6,252,057 B1
(45) Date of Patent: Jun. 26, 2001

(54) PROTEIN TARGETING TO GLYCOGEN

(75) Inventors: Matthew Jemail Brady; John Andrew Printen; Alan Robert Saltiel, all of Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/242,948

(22) PCT Filed: Aug. 22, 1997

(86) PCT No.: PCT/US97/14142

§ 371 Date: Feb. 25, 1999

§ 102(e) Date: Feb. 25, 1999

(87) PCT Pub. No.: WO98/08948

PCT Pub. Date: Mar. 5, 1998

Related U.S. Application Data

(60) Provisional application No. 60/025,107, filed on Aug. 30, 1996.

(51) Int. Cl.$^7$ .............................. C07H 21/04; C12N 5/00; C12N 15/00; C12N 15/09; C12N 15/63

(52) U.S. Cl. .................... 536/23.5; 435/325; 435/320.1; 530/350

(58) Field of Search ........................ 530/350; 435/320.1, 435/325; 536/23.5

(56) References Cited

PUBLICATIONS

M. Doherty, *FEBS Letters, Amino Acid Sequence and Expression of the Hepatic Glycogen–Binding (G1)–Subunit of Protein Phosphatase–1*, vol. 375, No. 3, 1995, pp. 295–298.

B. Nyomba, *J. Clin. Endocriniol. Metab, Immunoreactive Glycogen–Binding Subunit of Protein Phosphatase–1 In Human Skeletal Muscle*, XP 002047739, 1994, pp. 485–488.

D.F. Johnson, et al., *Eur. J. Biochem, Identification of Protein—Phosphatase–1–Binding Domains Ont He Glycogen and Myofibrillar Targetting Subunits*, XP002047740, 1996, pp. 317–325.

J.A. Printen, et al., *Science*, "PTG, A Protein phosphatase 1–Binding Protein With A Role In Glycogen Metabolism" XP002047741, vol. 275, 1997, pp. 1475–1478.

M.J. Brady, *J. Biol. Chem.*, "Role Of Protein Targetting To Glycogen (PTG) In The Regulation Of Protein Phosphatase–1 Activity", XP002047742, 1997, pp. 20198–20204.

PCT International Search Report, PCT/US97/14142.

*Primary Examiner*—Deborah J. R. Clark
*Assistant Examiner*—Eleanor Sorbello
(74) *Attorney, Agent, or Firm*—Charles W. Ashbrook

(57) ABSTRACT

The present invention provides human and murine genomic and complementary DNA and the proteins that are encoded by the DNA, which is called "Protein Targeting to Glycogen". Also provided is a method of increasing the amount of glycogen in a cell.

14 Claims, 9 Drawing Sheets

FIG-1

| | | | |
|---|---|---|---|
| PTG | 1 | MAMRICLAHSPPLKSFLGPYNGFQRRN | 31 |
| HepG1 | 1 | MAVDIEYSYSSMAPSLRRERFTFKISP | 27 |
| RG1 | 1 | MEPSEVPGQNSKDNFLEVPNLSDSLCE | 27 |
| Gac1 | 164 | NNEDCWFNDSSLVTNLLKNEKKFRYMN | 191 |

| | | | |
|---|---|---|---|
| PTG | 32 | LVNKLKPLKP--C--LSVKQEA-KSQSEWKSPH | 59 |
| HepG1 | 28 | KLN-KPLRP--CIQLGSKDEA-GRMVAPTVQE | 55 |
| RG1 | 28 | DEEVKAIFKPGFSPQPSRRGSE-SSEEVYVHTA | 59 |
| Gac1 | 192 | SLNNMFKLDLYDSEDEDDIDEHINSQAEYGYTY | 224 |

| | | | |
|---|---|---|---|
| PTG | 60 | NQAKKRVVFADSKGLSLTAIHVFSDLPEEPAWD | 92 |
| HepG1 | 56 | KKVKKRVSFADNQGLALTMVKVFSEF--DDPLD | 86 |
| RG1 | 60 | SSGGRRVSFADNFGFNLVSVKEF-----DTWE | 86 |
| Gac1 | 225 | NSLSTRGKTSENKSATSSLATQATNIC----D | 252 |

| | | | |
|---|---|---|---|
| PTG | 93 | LQFDLLDLNDISSSLKLHE-EKNLVFDFPQPST | 124 |
| HepG1 | 87 | IPFNITELLDNIVSLTAE-SESFVLDFPQPSA | 118 |
| RG1 | 87 | LPSVSTTFELGKDAFQTEEYVLSPLFDLPASKE | 119 |
| Gac1 | 253 | WKLHCTDLVPFKIAPPLFTKTLSASSDLQGQLT | 285 |

| | | | |
|---|---|---|---|
| PTG | 125 | DYLSFRDRFQKNFVCLENCSLEDRTVTGTVKVK | 157 |
| HepG1 | 119 | DYLDFRNRLQTNHVCLENCVLKEKAIAGTVKVQ | 151 |
| RG1 | 120 | DLMQ-QLQVQKAMLESTEYVPGSTSMKGIIRVL | 151 |
| Gac1 | 286 | KYLNGQN---VKLHSLTQLGDDSSKITGLVYVK | 315 |

| | | | |
|---|---|---|---|
| PTG | 158 | NVSFEKVQVRITFDTWKTYTDVDCVYMKNVYS | 190 |
| HepG1 | 152 | NLAFEKVVKIRMTFDTWKSFTDFPCQYVKDTYA | 184 |
| RG1 | 152 | NISFEKLVYVRMSLDDWQTHYDILAEYVPNSCD | 184 |
| Gac1 | 316 | NLSFEKYLEIKFTFNSWRDIHYVTANFNRTINS | 348 |

| | | | |
|---|---|---|---|
| PTG | 191 | SSDSDTFSFG------------IDLPRVIPTE | 210 |
| HepG1 | 185 | GSDRDTFSFD------------ISLPEKIQSY | 204 |
| RG1 | 185 | G-ETDQFSFK------------ISLVPPYQKD | 203 |
| Gac1 | 349 | NVDEFKFTIDLNSLKYILLIKRIITMEKNTSSC | 381 |

| | | | |
|---|---|---|---|
| PTG | 211 | E-KIEFCISYHANGRIFWDNNEGQNYRIVHVQW | 242 |
| HepG1 | 205 | E-RMEFAVCYECNGQSYWDSNKGKNYRITRAEL | 236 |
| RG1 | 204 | GSKVEFCIRYETSVGTFWSNNNGTNYTLVCQKK | 236 |
| Gac1 | 382 | PLNIELCCRYDVNNETYYDNNNGKNYHLFMTTF | 414 |

| | | | |
|---|---|---|---|
| PTG | 243 | KPDGVQTQ---VAPKDCAFQQGAPKTEIEPTVF | 272 |
| HepG1 | 237 | RSTQGMTE---PY--------NGPDFGISFDQF | 258 |
| RG1 | 237 | EPEPEPGK---PLEEAPSKQKKGC-LKVKSSKE | 265 |
| Gac1 | 415 | KKGGETKEKIPVVVEPASQTDAAMSPKEMKARF | 447 |

| | | | |
|---|---|---|---|
| PTG | 273 | GSPR--LASASSQSGRAGGEWRT | 293 |
| HepG1 | 259 | GSPRCSFGLFPEWPSYLGYEKLGPYY | 284 |
| RG1 | 266 | ESSETSEENNFENSKIADTYIPTIVC···· | 291 |
| Gac1 | 448 | VSSNPTLSRFLPQSRKFSEDTDYYNT···· | 472 |

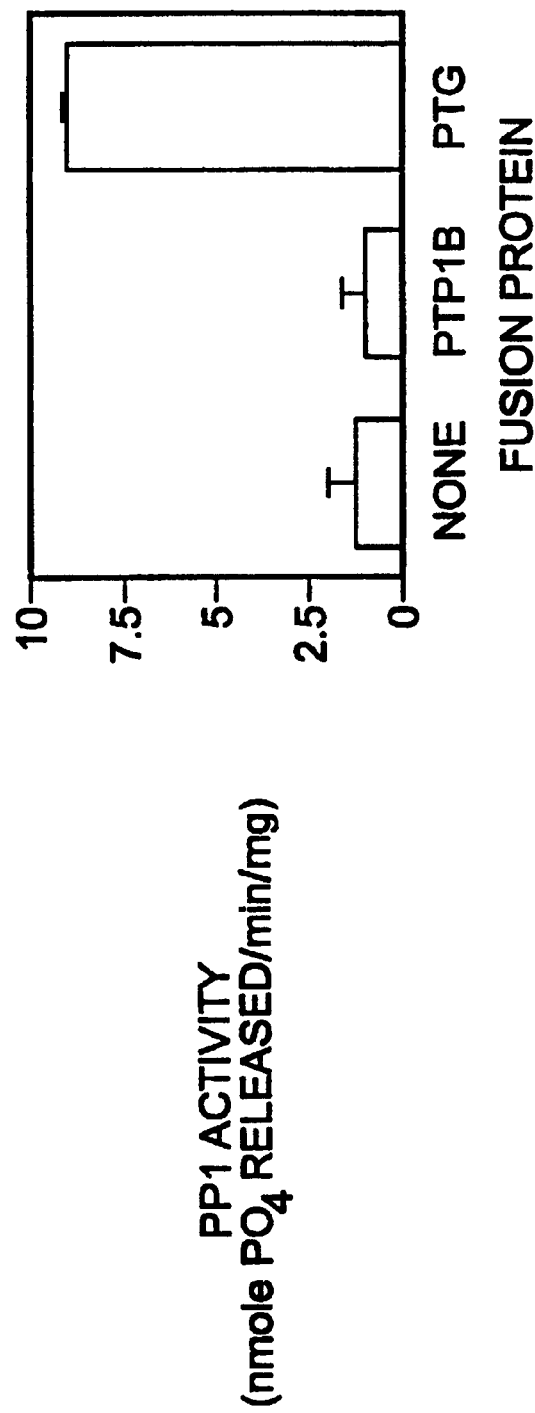
FIG-2D PP1 ACTIVITY IN GLYCOGEN PELLET

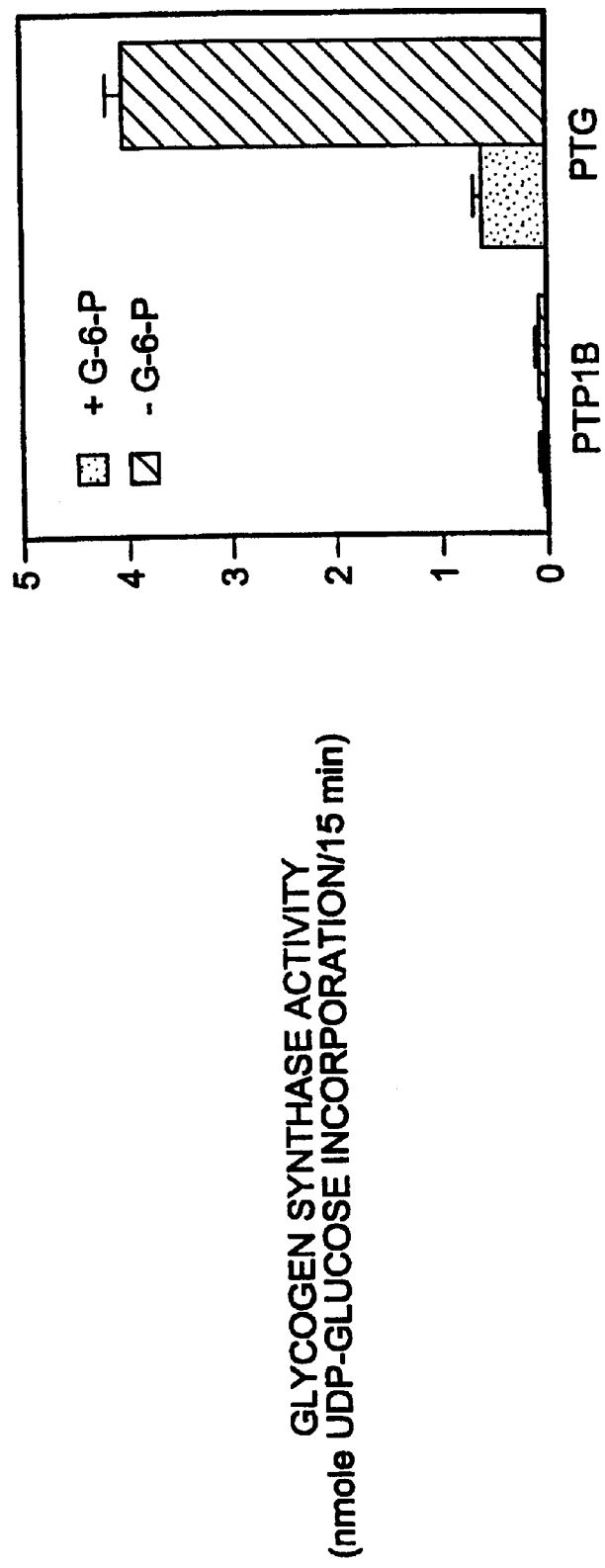
FIG-4B  PTG ASSOCIATED GLYCOGEN SYNTHASE ACTIVITY

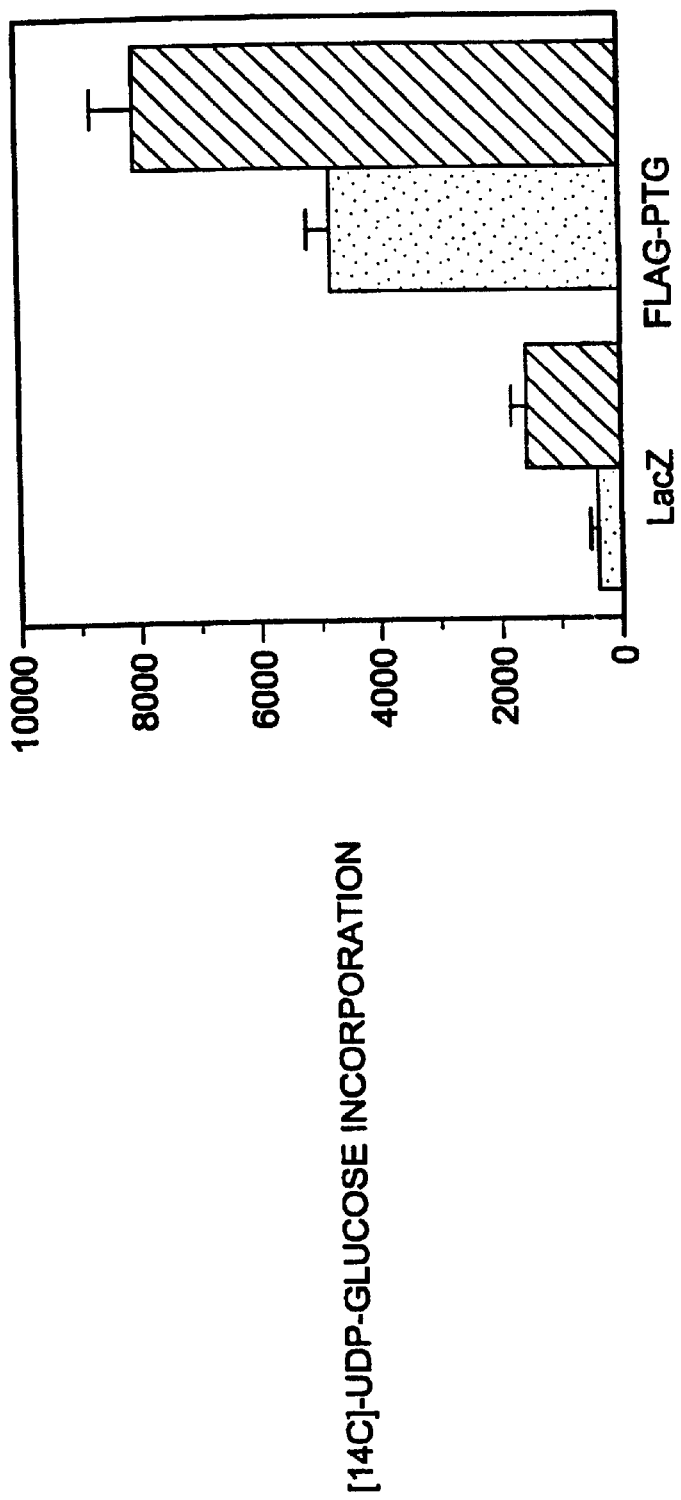
FIG-5 GLYCOGEN SYNTHESIS IN TRANSIENTLY TRANSFECTED CHO-IR CELLS

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 3461 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 2577..3461

(xi) SEQUENCE DESCRIPTION: SEQ ID NO: 1:

```
GGATCCCGCT GGCCCAGGGC TCAGGGACTC TACGGCCGCC TTCCAGCACG CTCTGGTCAC      60

ATCCAGCCCC GCGGTGATCA CGTTCCAGGG GCAGGGGCTC GTGCCCCAGC TGCACAGTGG     120

TTGGTCAGGG CGCACGGCCT TTGATTGGTC GGAGGGACCG GTTCACGTGA TCTGGCTTTG     180

ATAAGCTGCC TCCCGGTTGC CTGCGGTCAG TCGGCCGGCT GGACCGCGGC GCTGCATCCT     240

CTTAAGTACT GAGTGCGAAG TTGCTCAGGG TGCGGTTGTC GCGGTCGCCG CTGCCTCTCG     300

GTCCAATGAA CTGCACCAGG TAAGTTCAGT GCAACTCTGC GCCCGAATGG AGGGGAGCCT     360

GCAGCTGCGG GGACTTGGGG GCTTTTGTGG TTTTGTCTTC TCTGCAGATG GGAGACTCCC     420

AGGTTGATGG CTGAGTTGAA TCGTCCCGGA GGCTTGGAAG GGATGGAATT TGAGTTGAAT     480

TTCTTAGGCG CCTGTTTTGG GGAATCTAAC ATCTCAACAG TAGAAACTGC CTTAGTGAGT     540

CAGTTTTAGC TGGGATTCCT TTGCTGAAGT GACTCTGTTG CCTTTGAGCT CAAAGACCCA     600
```

-continued

```
AAAAATTGGG TTGCAGCTTA GTTTTATTGA TGAGGTAGTT TAGCCTGTGG CAAAAGGTAG      660

AGGATTTTGC ATTTCTTCTT TCCCCACTTC CCCTCTCCTG GTTTTGTCAT AAAAAAATGC      720

AGTCTTAGAG TTTGAGCAAG CTATTATTTT TAACTCCTGG CCAGGACTTA GGAATTCCAG      780

GGAAATAGCC CACTACTAAA ACTTTCTATA AATGCAGGAG TAAAAAAGGA AAAAAACCAA      840

AAAAACTAAA ACAAAAAGAA AAACAAGAAC AGCTCAACCA ATAAAAAACG AACAACAGCT      900

CCATCAACCA GGCAACCAAG ACCATCTCAC GAAATGTTGC ATCTCCAGTT GTAACTTAGT      960

CCAAGAATTC TCCCTCCCCA AATCCTGCCT CTTAATGGTT GTGAGACAAA TAGACTTTGA     1020

GGTTTTGTTG CTGGAAGTTT GTAATCCTCT CAGAAAAACC CTAGAGCTAT AAAGTGAGT      1080

TCAGTATACA TTCTTTACAG GCCACTTTGT GATGATGACC ATATACAGGG TGCTGTGCTT     1140

AGCACTGGTA TGAAGAGAAT TCTTCAAGCC AGACTATATT TATGATCAAA ATATGTTATA     1200

TACATATATA AACTGTTAAA GAATAAATAA TTAATAAAGC CCCAGACTCC AAAATGGCAC     1260

CTACTGTATT TCATGTTTCT TTGATTTATA AGGCTGACAT TGGAGAGGAA AAACCTAATT     1320

CTGTAAGTGT GGAATTATAG TGTGGTTCAA GGGAAAGAAA GGCCAGAAAA GTCTTGATGG     1380

ATGGTTCTTT GTTTGATGCA AACTATTGTT ATTGCCTTCC TACTTGTAAA TAGGACCTGC     1440

TCAACAACAG GAAACATCAT AGAAGCCCAA ACCAGTAGAT GCTATAATCC ATCAGTCAAA     1500

GATAATGAAC ATCTTAGTGT TTCCTTTGTA GTTTCAGTAT TTATAAATCA TATATCTTCA     1560

GTGTATTTTA AAACAGCTCA TTTCTGGTTA TCAGTTTTTA AAACTACTTT ATGTTGTGTA     1620

TATATAATGT ACACTGCAGG CTACAAGACA GAGCTATAGT AAAGTGGTTA TTACTGGTCA     1680

GAATGAACAA TCTGTTATCC CTGCAGGTTA GCTATTCCCT TTATAGTTGG ACCTGTCATG     1740

GGCATCTTTC CTATATGAAC TGTCAGATTG TTTAAAGTTT TTCCTTTAGT CTGTGAGATG     1800

TTGGCTGGTG TTGCAGTTGG TCATTTGTGA AAAAATGAGG ATGACTGTGA TAAAATGAAA     1860

AAGTCATTCT TTCTTTTAAC AAGCGTCACC TACTGTCACT CTAAGGACAG CATGACATTT     1920

TAAGAATTGC TTCATTTATT GTTTCCCAAG TGGATTACTT CTCCTGAGAA GTAAAACCGG     1980

TTCGAGAGCC AAAATAGGAA ACAGCAGCCA GAGGGAGCGA GAGGCTGGGA CTGTGATAAT     2040

GGAAGAAGCT GTCTGGCCAA TGGACTCTTT TGGGGGAAGC TTTAAGAACA TATTTACCTT     2100

TCTGGCTCCA TGCCATGAAG CTCTACTGTA GTGGTTTTAA GTCCCCGGAA TCTGAATTTT     2160

TTTTTTCTAA AGGAAAGAAA CTTCTCAGGT CTTGTTGATC TGACAGGTTT AAGAACCACT     2220

GGCCCAGAAC AGAGTACATA ATTCCAAGAG CTGTGTCAGA CTTGTTCAGA TAGAGCCCTC     2280

TTGTTTCTCA GATGGAGAAA CTGAATCCTC TCTGAGTGTT TCAGGCAGTT TACACATGGG     2340

CCCAGCAGCC TGCCAAGCAC AGAGCTAGAC TGTAGATCTC ATCACCCCAG TGCTCTCCTT     2400

TTCTCCACGT GATAGCACCT CTCTGCACTG GAGTACTAGT GTGTGTGCAT TTGGGACCAG     2460

GGGAAGACGA CTCCAGACCT CGGTGATTAC CACTGTTTTT TTTTTTTTT TCTCATTCCA      2520

GAATGATCCA TGTGCTAGAT CCACGTCCTT TGACAAGTTC CGTCATGCCC GTGGAC          2576

ATG GCC ATG AGG ATT TGC TTG GCT CAT TCA CCA CCT CTG AAG AGT TTC       2624
Met Ala Met Arg Ile Cys Leu Ala His Ser Pro Pro Leu Lys Ser Phe
  1               5                  10                  15

CTG GGT CCT TAC AAT GGT TTT CAA CGA AGA AAT TTT GTG AAT AAA TTG       2672
Leu Gly Pro Tyr Asn Gly Phe Gln Arg Arg Asn Phe Val Asn Lys Leu
                 20                  25                  30

AAA CCT TTG AAA CCA TGT CTC AGT GTC AAG CAG GAA GCC AAA TCG CAG       2720
Lys Pro Leu Lys Pro Cys Leu Ser Val Lys Gln Glu Ala Lys Ser Gln
         35                  40                  45

AGT GAG TGG AAG AGC CCA CAC AAC CAA GCC AAG AAG CGG GTC GTG TTT       2768
```

```
Ser Glu Trp Lys Ser Pro His Asn Gln Ala Lys Lys Arg Val Val Phe
     50                  55                  60

GCG GAC TCC AAG GGG CTG TCA CTC ACT GCT ATC CAT GTC TTC TCC GAC   2816
Ala Asp Ser Lys Gly Leu Ser Leu Thr Ala Ile His Val Phe Ser Asp
 65              70                  75                  80

CTT CCA GAA GAA CCA GCG TGG GAC CTG CAG TTT GAT CTC TTG GAC CTT   2864
Leu Pro Glu Glu Pro Ala Trp Asp Leu Gln Phe Asp Leu Leu Asp Leu
                 85                  90                  95

AAC GAT ATC TCC TCC AGC TTA AAA CTT CAC GAG GAG AAA AAT TTG GTT   2912
Asn Asp Ile Ser Ser Ser Leu Lys Leu His Glu Glu Lys Asn Leu Val
                100                 105                 110

TTT GAT TTT CCC CAG CCC TCA ACC GAC TAC TTA AGT TTC CGG GAC CGC   2960
Phe Asp Phe Pro Gln Pro Ser Thr Asp Tyr Leu Ser Phe Arg Asp Arg
            115                 120                 125

TTT CAG AAG AAC TTT GTC TGC CTC GAG AAC TGC TCT TTG GAA GAT CGG   3008
Phe Gln Lys Asn Phe Val Cys Leu Glu Asn Cys Ser Leu Glu Asp Arg
130                 135                 140

ACG GTG ACC GGG ACA GTG AAA GTG AAG AAT GTG AGC TTT GAG AAG AAG   3056
Thr Val Thr Gly Thr Val Lys Val Lys Asn Val Ser Phe Glu Lys Lys
145                 150                 155                 160

GTT CAG GTC CGG ATC ACC TTT GAC ACC TGG AAA ACC TAC ACA GAT GTG   3104
Val Gln Val Arg Ile Thr Phe Asp Thr Trp Lys Thr Tyr Thr Asp Val
                165                 170                 175

GAC TGT GTC TAC ATG AAG AAT GTT TAC AGC AGC TCA GAC AGC GAC ACC   3152
Asp Cys Val Tyr Met Lys Asn Val Tyr Ser Ser Ser Asp Ser Asp Thr
            180                 185                 190

TTC TCC TTT GCA ATC GAC TTG CCC CGT GTC ATT CCA ACT GAG GAG AAA   3200
Phe Ser Phe Ala Ile Asp Leu Pro Arg Val Ile Pro Thr Glu Glu Lys
            195                 200                 205

ATT GAG TTC TGC ATT TCT TAT CAC GCT AAT GGG AGG ATC TTC TGG GAC   3248
Ile Glu Phe Cys Ile Ser Tyr His Ala Asn Gly Arg Ile Phe Trp Asp
210                 215                 220

AAC AAT GAG GGT CAG AAT TAC AGA ATT GTC CAT GTG CAA TGG AAA CCT   3296
Asn Asn Glu Gly Gln Asn Tyr Arg Ile Val His Val Gln Trp Lys Pro
225                 230                 235                 240

GAC GGA GTG CAG ACT CAG GTG GCA CCC AAA GAC TGT GCA TTC CAA CAG   3344
Asp Gly Val Gln Thr Gln Val Ala Pro Lys Asp Cys Ala Phe Gln Gln
                245                 250                 255

GGG CCC CCT AAG ACT GAG ATA GAG CCC ACA GTC TTT GGC AGT CCA AGG   3392
Gly Pro Pro Lys Thr Glu Ile Glu Pro Thr Val Phe Gly Ser Pro Arg
            260                 265                 270

CTT GCT AGC GGC CTC TTC CCA GAG TGG CAG AGC TGG GGG AGA GTG GAG   3440
Leu Ala Ser Gly Leu Phe Pro Glu Trp Gln Ser Trp Gly Arg Val Glu
            275                 280                 285

AAC TTG ACC TCC TAT CGA TGA                                       3461
Asn Leu Thr Ser Tyr Arg  *
            290                 295

(2) INFORMATION FOR SEQ ID NO: 2:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Met Arg Ile Cys Leu Ala His Ser Pro Pro Leu Lys Ser Phe
 1               5                  10                  15

Leu Gly Pro Tyr Asn Gly Phe Gln Arg Arg Asn Phe Val Asn Lys Leu
```

```
                    20                      25                      30
Lys Pro Leu Lys Pro Cys Leu Ser Val Lys Gln Glu Ala Lys Ser Gln
                35                      40                      45

Ser Glu Trp Lys Ser Pro His Asn Gln Ala Lys Lys Arg Val Val Phe
 50                      55                      60

Ala Asp Ser Lys Gly Leu Ser Leu Thr Ala Ile His Val Phe Ser Asp
 65                      70                      75                      80

Leu Pro Glu Glu Pro Ala Trp Asp Leu Gln Phe Asp Leu Leu Asp Leu
                85                      90                      95

Asn Asp Ile Ser Ser Leu Lys Leu His Glu Lys Asn Leu Val
                100                     105                     110

Phe Asp Phe Pro Gln Pro Ser Thr Asp Tyr Leu Ser Phe Arg Asp Arg
                115                     120                     125

Phe Gln Lys Asn Phe Val Cys Leu Glu Asn Cys Ser Leu Glu Asp Arg
                130                     135                     140

Thr Val Thr Gly Thr Val Lys Val Lys Asn Val Ser Phe Glu Lys Lys
145                     150                     155                     160

Val Gln Val Arg Ile Thr Phe Asp Thr Trp Lys Thr Tyr Thr Asp Val
                165                     170                     175

Asp Cys Val Tyr Met Lys Asn Val Tyr Ser Ser Ser Asp Ser Asp Thr
                180                     185                     190

Phe Ser Phe Ala Ile Asp Leu Pro Arg Val Ile Pro Thr Glu Glu Lys
                195                     200                     205

Ile Glu Phe Cys Ile Ser Tyr His Ala Asn Gly Arg Ile Phe Trp Asp
                210                     215                     220

Asn Asn Glu Gly Gln Asn Tyr Arg Ile Val His Val Gln Trp Lys Pro
225                     230                     235                     240

Asp Gly Val Gln Thr Gln Val Ala Pro Lys Asp Cys Ala Phe Gln Gln
                245                     250                     255

Gly Pro Pro Lys Thr Glu Ile Glu Pro Thr Val Phe Gly Ser Pro Arg
                260                     265                     270

Leu Ala Ser Gly Leu Phe Pro Glu Trp Gln Ser Trp Gly Arg Val Glu
                275                     280                     285

Asn Leu Thr Ser Tyr Arg
                290

(2) INFORMATION FOR SEQ ID NO: 3:

(i) SEQUENCE CHARACTERISTICS:
        (A) LENGTH: 5789 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 4238..5176

(xi) SEQUENCE DESCRIPTION: SEQ ID NO: 3:

CTTGACCTGT CTAAGCTTTC AGTTCCTCAT CTGTGAAATA AAGAGTTTGA TGCCTATCAC      60

CTCCTACCTC CATAATTCTA ACCATTGATG GGTCATTAAA ATAAGACAAT ATGGTGCAGC     120

GGTTATTGCT CTGGTATCAG CCAGGCTCTA ATCCCTGCTC TACCTGTGAG AACCTGGGCA    180

GGTTTTTTTT TTGTTTTTTG TTTTCGAGAT AGAGTCTCGC TCTGTTGCCC AGGCTGGAGT    240

GCAGTGGTGC AATCTCAGCT CACTGCAACC TCCGCCTCCC GGGTTCAAGC GATTCTCCTG    300
```

```
CCTCAGCCTC CAGAGTAGCT GAGAGTACAG GTGTGCACCA CCATGCCCGG CTAATTTTTG    360

TATTTTTAGT AGAGATAGGG TTTCACCATG TTGGCCAGGC TGGTCTTGAA CTCCTGGCCT    420

CAAGTGATCC ACTGGGCAGA TTTCCTGACC ATTCAGTGTC TCCGTTTTCT TTTCTCTAAA    480

ATGGGATTAA TAACTGGACA TATCACATAG GGTTGTTGTG AGGATTGAAT TGATAGCACA    540

TAGTGTTTGG CACAGAGTAA AGGCTCAACA AGCAGCAGCT ATTCTCAATA TTTTAGCTCA    600

GGCACCAGGC GCCTTGAGGT GATAGAGTAA AAACTCTAGC TGAGAGATCA AGTAGAAACT    660

TGGGAACTAG CCCGGGTGGA ACACAGGCAC TGGGCATCGT GCTGAGTCTG TTCATTGGCA    720

CCATCTTACT TCATCTTCAG AACGTTACTA TCTCTGTTTT ACACATGAGG AAACTGAGGT    780

TAGAACTTGC CTAGTTCGGT AGCTAGTAAG TGTCAATCCA AAGACCTTCC AGCTAGTTTT    840

GGTTGAGCTA AAGGGGCTAG AAGACCTGCC ATTAGTTAGA TATTTCATTT CAAAAATAAA    900

ACCCAGGCAT GAAGTCCCTT TCCCAGTGAT ATTCAGTGTG ATTTTTTTCT TCACTCTAAT    960

AATTTTAACA ATTCCACTGT TTGACAGTTG TTTAAAAGAC ATAGGAATTT TTGTATATTT   1020

TAATTGACTA ATGGATAGCT CAATTAGGGG AGCAAAACTA GGATGTGGGT TTTATAAAAA   1080

TAATTTAGAC TTGACTTAGA CATTTAATTT TACAGTTGTA AATGATGGTC TAAAAATTCT   1140

TCAAACTAAT CAAAATAATG AAACTTCAGC GAAAGTGAGT GGCTCAGAAG GCCCATGAAA   1200

CATACGGCGT GATTTTTTAA ATTTTATTTT AACATTTTGA TTTCCACACC ACTGCCAAAG   1260

GACGTCAGAA TTGAGTAAGG GGTTTGGGTT GACTGCTGCC TCTTGACCGG CTGTATGTGT   1320

GAAAAGGGTC ATTTCACTTC CGGCTTTAGT GTTCCCCGCA GGGGAGAAAA TTGAAGAATA   1380

GACAGAAATA CGAAGTGTCT TTTAATTAAA TGCCACCTTG GTGTTTTATG GGGCTCGTAT   1440

GCTTTCCTAA CAACATTTGT TAGATAAGTT GGTAATTCCC GGCAGCTGTC TACTGTGTGG   1500

TGCATCTGTG AACTCATACT AATCGAAAAG CATGCAGCCA GTTTGGGATC GCGCAGGCTA   1560

AGGTGAGGGA GAAATGCGGA TACACCGGGT AATGAACGAT ATAAACATTT CAAATGCGAT   1620

ACACATTCGG TTTGAGCCAC ATCTTCTGTG TGCAGATTCA CCCGCAGTGA CCCACAAAGC   1680

TATTCCCAAG TAACAGCCGC CCCAAGCCTG AGGCACTGGC GCCCGCCTG  GGCGAGGCTG   1740

GCTGCGCTCT CTCTTGGCCG GCGCCCGCTG CATGCGGTAC GTGCCTGCCC GGCCCCTAGC   1800

CCAGGGTTCC CGTTACGCGG CTGGTTCCAG CTGGCCGCGG AGTCCCAGAA CCTCCCCGGG   1860

ATGCCCAGAT AGCTCTCTGC ACGTCTGGCC CCGGGGCGAT CACGTTGCCG GGGCGAGGGC   1920

TGGCGCCCCA GCTGGGCGCT GGTTGGTCGC GCCCTGGGGC TCGAGGCCCG GCGATTGGTC   1980

CCAGGGATCG GGTCACGTGC TTGGGAGCAG ATAAGCGGCC TCTAGGCGCC GGGCCCTCAG   2040

TCTCTCCCAG CGACCGCCGC GGGGGCAAGG CCTGGAGCTG TGGTTCGAAT TTGTGCAGGC   2100

AGCGGGTGCT GGCTTTTAGG GTCCGCCGCC TCTCTGCCTA ATGAGCTGCA CCAGGTAGGT   2160

TCGCTGCAAC TCTGCGCGCT AGGAACACAG GGAACGCGC  AGCTGTGGGG AAGTTGGGGG   2220

GCGTTTCAGT TCTATCATCT CTGGAAATGG ACACCCCAGG GGGAGGACAA GTGGACTGAC   2280

TGCGTAGTTG AATCTGGCAA CCGAGAGGCC TTGGAGGTGT AGAAATTTGG CTCTATTTCT   2340

TAAGCAGAGC CTATTTTAGT AATCAGCATC TTAAAGCAGA AATTATCTTA ACGTGAATCA   2400

GCTTGAGTTA GGATTTTCTC ATGGATGCGG CTGTTCTTTT GGTCCTGCAC AAATGTCCCA   2460

AAGACTCGGG CAGCTGAAGT GGTGAGAACA GCACTCTGAC ATTGCTGGTT AGGTGGTTTA   2520

GCTTGGAGGA AAAAAATTAC AGGACGACGT TTGCATTCAT TCGTCCTTCT TATCACAGTT   2580

TGCCATAGCA AAATCTCAAG AGTTTGAGCA AACGATTACT TTTAACTCTT GTCCAGGACT   2640
```

```
                                                          -continued

TAAAGTTCCA AGGAAATCAC CCAAACTAAA ACTGTCTTTC TATAAATGCA AAAAGTAAAA    2700

AAAAAAAAAC AAAAAAACCA AAAAAAACCT CCCATAAAAC TACTTTAAAT AGCTTCTCCA    2760

GACATAGCTT AGCAGAAGAT TCTCTAAAAA TCCTGCCTAT TAACTATTAT TAGACCCACA    2820

AATATAGCTT TAGCTTTCAT TTGTTTGTTT AAGTTTGCAG ATCTCCCAGA AAAACCCCAG    2880

AGCTAACACA GTAAATTCTG CGAGTGTTAT TACACACTTT TGTGATAATG ACCACTTGCA    2940

TACATGTTTA GAGCTGCTGT GAGGAGAGTT ACTAAAGCCA GACTGAGAAA TGTCGTGTAC    3000

AGTATACACA CACCTCTTAC TTGTAAGGCT AAGATAGGGA AAAAAATCTT AATACCATAA    3060

GCTTGGAAAT ATATGATGAG GGCTAAAGGT CAGAGAAAAG TCTTCTTTAT AGATGCTTCT    3120

TGGTTTAATA TTGCTGAGCA TAGTCATGTT TAAAACTTTA AATGGTTTTA TTGTCTTTCT    3180

ACTTATAAAT GTCTATTAGA AAATGCCAAA AAAGAACAAA AACGAAAATA GATAATCTAT    3240

AATCCTATCA CCCAGAAATA ATAATTATTA AATTATTAGG AAAGGTGTAT TTCCTATAGA    3300

GTTTTTCAAT ATTTATAAGT TTGTATATAT AAAATGTATA TTTTAAAACA CTCCAACTTT    3360

CAGGTAATCA GTTTTTCCAC TTAAATGTGG ACTTGTCATG GGCATCTCTT TAGGTGAATT    3420

ATCAATTATA TAGTTTTTAA GTGCATATGA ATTGTTGGCT TGTATTTCAG TGGTTATTTG    3480

TGAAAAATAA GAGCATGATA ATCAAAGTGC AAAGATGATT CTTTGACTTC TTCTCTAGCC    3540

TTCTCACTTT CAAAACTGCA TGTTATTTTT TTTTTTCAAG TGAATTACCT TACCAGAGAA    3600

GTGTCAATCA ATTTAGCAGC AAAATAAGCC AACGTAGCCA GAGGGAGCAG AGGGTCTGGA    3660

ACTGTGGCTC CTGAACCTGT CTGGTCATTA GAATCACCTG GGAAGCTTTA AGAACATACC    3720

CATCCCTTGG CCCTAGCCCC AGAAGTTCTG CCTCAGTAGT TCTGAGTCCC AGGAATTGGA    3780

AAGAAAGAAG AAAGAGAAAG AGAGAGAGAG AGGAAGAAAG GAAGGAAGGA GGGAAGGAGG    3840

AAAGGAGGAA AGACAAGAAA GAAAGAAAAT GAATTCCCTA GACATAGTGA CCAGACAGGT    3900

TTGAGGACCA CTGGTCCAGA ACAGAGCACA CAGTTCTCAA GGCTGCCTTG GAGATAATCA    3960

AATCGAACCC TTTTATTTCT CAGATGGGGA AACTGAGACC CCCATCACCC TCTAAGTGTT    4020

TTAAGCAATT AATAGCCTTT ACCGGCCAAG GGTAGAGGTA GACATAGAAG ATCTGATCAC    4080

TTAATACTGT TCTCTTTTAC TACATATGAT AGCACCTGCC TGATATCTAG TGCACTGGCT    4140

ATAATTCAGT CAGCACAAAA ATAGTACATA TGTATTTGGC ACTGGGGAAG AGCATTTCCG    4200

ATCCAGGTGA TAATCCCTCT TCTTTTTGCA TTCCAGA ATG ATC CAG GTT TTA GAT    4255
                                        Met Ile Gln Val Leu Asp
                                                              300

CCA CGT CCT TTG ACA AGT TCG GTC ATG CCC GTG GAT GTG GCC ATG AGG    4303
Pro Arg Pro Leu Thr Ser Ser Val Met Pro Val Asp Val Ala Met Arg
        305                 310                 315

CTT TGC TTG GCA CAT TCA CCA CCT GTG AAG AGT TTC CTG GGC CCG TAC    4351
Leu Cys Leu Ala His Ser Pro Pro Val Lys Ser Phe Leu Gly Pro Tyr
        320                 325                 330

GAT GAA TTT CAA CGA CGA CAT TTT GTG AAT AAA TTA AAG CCC CTG AAA    4399
Asp Glu Phe Gln Arg Arg His Phe Val Asn Lys Leu Lys Pro Leu Lys
        335                 340                 345

TCA TGT CTC AAT ATA AAA CAC AAA GCC AAA TCA CAG AAT GAC TGG AAG    4447
Ser Cys Leu Asn Ile Lys His Lys Ala Lys Ser Gln Asn Asp Trp Lys
350                 355                 360                 365

TGC TCA CAC AAC CAA GCC AAG AAG CGC GTT GTG TTT GCT GAC TCC AAG    4495
Cys Ser His Asn Gln Ala Lys Lys Arg Val Val Phe Ala Asp Ser Lys
                370                 375                 380

GGC CTC TCT CTC ACT GCG ATC CAT GTC TTC TCC GAC CTC CCA GAA GAA    4543
Gly Leu Ser Leu Thr Ala Ile His Val Phe Ser Asp Leu Pro Glu Glu
            385                 390                 395
```

```
CCA GCG TGG GAT CTG CAG TTT GAT CTC TTG GAC CTT AAT GAT ATC TCC        4591
Pro Ala Trp Asp Leu Gln Phe Asp Leu Leu Asp Leu Asn Asp Ile Ser
            400                 405                 410

TCT GCC TTA AAA CAC CAC GAG GAG AAA AAC TTG ATT TTA GAT TTC CCT        4639
Ser Ala Leu Lys His His Glu Glu Lys Asn Leu Ile Leu Asp Phe Pro
        415                 420                 425

CAG CCT TCA ACC GAT TAC TTA AGT TTC CGG AGC CAC TTT CAG AAG AAC        4687
Gln Pro Ser Thr Asp Tyr Leu Ser Phe Arg Ser His Phe Gln Lys Asn
430                 435                 440                 445

TTT GTC TGT CTG GAG AAC TGC TCG TTG CAA GAG CGA ACA GTG ACA GGG        4735
Phe Val Cys Leu Glu Asn Cys Ser Leu Gln Glu Arg Thr Val Thr Gly
                450                 455                 460

ACT GTT AAA GTC AAA AAT GTG AGT TTT GAG AAG AAA GTT CAG ATC CGT        4783
Thr Val Lys Val Lys Asn Val Ser Phe Glu Lys Lys Val Gln Ile Arg
            465                 470                 475

ATC ACT TTC GAT TCT TGG AAA AAC TAC ACT GAC GTA GAC TGT GTC TAT        4831
Ile Thr Phe Asp Ser Trp Lys Asn Tyr Thr Asp Val Asp Cys Val Tyr
        480                 485                 490

ATG AAA AAT GTG TAT GGT GGC ACA GAT AGT GAT ACC TTC TCA TTT GCC        4879
Met Lys Asn Val Tyr Gly Gly Thr Asp Ser Asp Thr Phe Ser Phe Ala
495                 500                 505

ATT GAC TTA CCC CCT GTC ATT CCA ACT GAG CAG AAA ATT GAG TTC TGC        4927
Ile Asp Leu Pro Pro Val Ile Pro Thr Glu Gln Lys Ile Glu Phe Cys
510                 515                 520                 525

ATT TCT TAC CAT GCT AAT GGG CAA GTC TTT TGG GAC AAC AAT GAT GGT        4975
Ile Ser Tyr His Ala Asn Gly Gln Val Phe Trp Asp Asn Asn Asp Gly
                530                 535                 540

CAG AAT TAT AGA ATT GTT CAT GTT CAA TGG AAG CCT GAT GGG GTG CAG        5023
Gln Asn Tyr Arg Ile Val His Val Gln Trp Lys Pro Asp Gly Val Gln
            545                 550                 555

ACA CAG ATG GCA CCC CAG GAC TGT GCA TTC CAC CAG ACG TCT CCT AAG        5071
Thr Gln Met Ala Pro Gln Asp Cys Ala Phe His Gln Thr Ser Pro Lys
        560                 565                 570

ACA GAG TTA GAG TCA ACA ATC TTT GGC AGT CCG AGG CTG GCT AGT GGG        5119
Thr Glu Leu Glu Ser Thr Ile Phe Gly Ser Pro Arg Leu Ala Ser Gly
575                 580                 585

CTC TTC CCA GAG TGG CAG AGC TGG GGG AGA ATG GAG AAC TTG GCC TCT        5167
Leu Phe Pro Glu Trp Gln Ser Trp Gly Arg Met Glu Asn Leu Ala Ser
590                 595                 600                 605

TAT CGA TGA ATTAAGCAAC AATGTAACTG GTCTTGACTT GTCATATTCC                5216
Tyr Arg *

CCCATGCAAT CCTAGGTCTG TATTGCTCAA TTTTAGGAAG CCTTTGCTAC TCCATCAGTA      5276

GGTTTAGATT TGAGCTTTTG AAACCTGGCT ATGGAAAAGA AAGACACTTG AGAATTTATG      5336

TTGGGGTCTG TACAGATAAA TGCTAACCCA ATTTGGCTTT GAAGGATCAA GTAACAGGTT      5396

GAAAACTATT TTTATAAAGG TAATACTTTT TCAGTTCCCT TCTTCCTTCC CTCTCAATCC      5456

ACTAGCTTTC ATGTTGGGCA AGGAAAAGTT GAGGAAGGAT GGCTGATGGT GATGGAAAGC      5516

TATGTTAATG GTATGAGGAA TGTGTGAAAA GTATACACAA AGGGCTCTGA AGCTCAAGTC      5576

AGAGGAGTGG GAGGTCTGAT CATTGTTGGT GGAAAAACGT AAGGTTATTT TGTGTTTTTA      5636

AGTTGGTTTT ACAATTCTTT CCTGGGGAAA TTATTTCTGG AGGGGAAAAA GATCCATTCT      5696

ACGTATCCTT GTGGAGAAAA GCTAAATAAC CTTTAAGAAT GTGGGTGGTA TTGGAGAAAG      5756

AAGATGAATT ATAGCTCCGG AGAATCAAGA TCT                                   5789

(2) INFORMATION FOR SEQ ID NO: 4:
```

(i) SEQUENCE CHARACTERISTICS:
    (A) LENGTH: 312 amino acids
    (B) TYPE: amino acid
    (D) TOPOLOGY: linear (ii) MOLECULE TYPE: protein (xi) SEQUENCE DESCRIPTION: SEQ ID NO: 4:

```
Met Ile Gln Val Leu Asp Pro Arg Pro Leu Thr Ser Ser Val Met Pro
 1               5                  10                  15

Val Asp Val Ala Met Arg Leu Cys Leu Ala His Ser Pro Pro Val Lys
            20                  25                  30

Ser Phe Leu Gly Pro Tyr Asp Glu Phe Gln Arg Arg His Phe Val Asn
        35                  40                  45

Lys Leu Lys Pro Leu Lys Ser Cys Leu Asn Ile Lys His Lys Ala Lys
    50                  55                  60

Ser Gln Asn Asp Trp Lys Cys Ser His Asn Gln Ala Lys Lys Arg Val
65                  70                  75                  80

Val Phe Ala Asp Ser Lys Gly Leu Ser Leu Thr Ala Ile His Val Phe
                85                  90                  95

Ser Asp Leu Pro Glu Glu Pro Ala Trp Asp Leu Gln Phe Asp Leu Leu
            100                 105                 110

Asp Leu Asn Asp Ile Ser Ser Ala Leu Lys His His Glu Glu Lys Asn
        115                 120                 125

Leu Ile Leu Asp Phe Pro Gln Pro Ser Thr Asp Tyr Leu Ser Phe Arg
    130                 135                 140

Ser His Phe Gln Lys Asn Phe Val Cys Leu Glu Asn Cys Ser Leu Gln
145                 150                 155                 160

Glu Arg Thr Val Thr Gly Thr Val Lys Val Lys Asn Val Ser Phe Glu
                165                 170                 175

Lys Lys Val Gln Ile Arg Ile Thr Phe Asp Ser Trp Lys Asn Tyr Thr
            180                 185                 190

Asp Val Asp Cys Val Tyr Met Lys Asn Val Tyr Gly Gly Thr Asp Ser
        195                 200                 205

Asp Thr Phe Ser Phe Ala Ile Asp Leu Pro Pro Val Ile Pro Thr Glu
    210                 215                 220

Gln Lys Ile Glu Phe Cys Ile Ser Tyr His Ala Asn Gly Gln Val Phe
225                 230                 235                 240

Trp Asp Asn Asn Asp Gly Gln Asn Tyr Arg Ile Val His Val Gln Trp
                245                 250                 255

Lys Pro Asp Gly Val Gln Thr Gln Met Ala Pro Gln Asp Cys Ala Phe
            260                 265                 270

His Gln Thr Ser Pro Lys Thr Glu Leu Glu Ser Thr Ile Phe Gly Ser
        275                 280                 285

Pro Arg Leu Ala Ser Gly Leu Phe Pro Glu Trp Gln Ser Trp Gly Arg
    290                 295                 300

Met Glu Asn Leu Ala Ser Tyr Arg
305                 310
```

(2) INFORMATION FOR SEQ ID NO: 5:

(i) SEQUENCE CHARACTERISTICS:
        (A) LENGTH: 885 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
ATGGCCATGA GGATTTGCTT GGCTCATTCA CCACCTCTGA AGAGTTTCCT GGGTCCTTAC    60
AATGGTTTTC AACGAAGAAA TTTTGTGAAT AAATTGAAAC CTTTGAAACC ATGTCTCAGT   120
GTCAAGCAGG AAGCCAAATC GCAGAGTGAG TGGAAGAGCC ACACAACCA  AGCCAAGAAG   180
CGGGTCGTGT TTGCGGACTC CAAGGGGCTG TCACTCACTG CTATCCATGT CTTCTCCGAC   240
CTTCCAGAAG AACCAGCGTG GGACCTGCAG TTTGATCTCT TGGACCTTAA CGATATCTCC   300
TCCAGCTTAA AACTTCACGA GGAGAAAAAT TTGGTTTTTG ATTTTCCCCA GCCCTCAACC   360
GACTACTTAA GTTTCCGGGA CCGCTTTCAG AAGAACTTTG TCTGCCTCGA GAACTGCTCT   420
TTGGAAGATC GGACGGTGAC CGGGACAGTG AAAGTGAAGA ATGTGAGCTT TGAGAAGAAG   480
GTTCAGGTCC GGATCACCTT TGACACCTGG AAAACCTACA CAGATGTGGA CTGTGTCTAC   540
ATGAAGAATG TTTACAGCAG CTCAGACAGC GACACCTTCT CCTTTGCAAT CGACTTGCCC   600
CGTGTCATTC AACTGAGGA  GAAAATTGAG TTCTGCATTT CTTATCACGC TAATGGGAGG   660
ATCTTCTGGG ACAACAATGA GGGTCAGAAT TACAGAATTG TCCATGTGCA ATGGAAACCT   720
GACGGAGTGC AGACTCAGGT GGCACCCAAA GACTGTGCAT TCCAACAGGG GCCCCCTAAG   780
ACTGAGATAG AGCCCACAGT CTTTGGCAGT CCAAGGCTTG CTAGCGGCCT CTTCCCAGAG   840
TGGCAGAGCT GGGGGAGAGT GGAGAACTTG ACCTCCTATC GATGA                  885
```

(2) INFORMATION FOR SEQ ID NO: 6:

(i) SEQUENCE CHARACTERISTICS:
        (A) LENGTH: 939 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
ATGATCCAGG TTTTAGATCC ACGTCCTTTG ACAAGTTCGG TCATGCCCGT GGATGTGGCC    60
ATGAGGCTTT GCTTGGCACA TTCACCACCT GTGAAGAGTT TCCTGGGCCC GTACGATGAA   120
TTTCAACGAC GACATTTTGT GAATAAATTA AAGCCCCTGA ATCATGTCT  CAATATAAAA   180
CACAAAGCCA AATCACAGAA TGACTGGAAG TGCTCACACA ACCAAGCCAA GAAGCGCGTT   240
GTGTTTGCTG ACTCCAAGGG CCTCTCTCTC ACTGCGATCC ATGTCTTCTC CGACCTCCCA   300
GAAGAACCAG CGTGGGATCT GCAGTTTGAT CTCTTGGACC TTAATGATAT CTCCTCTGCC   360
TTAAAACACC ACGAGGAGAA AAACTTGATT TTAGATTTCC CTCAGCCTTC AACCGATTAC   420
TTAAGTTTCC GGAGCCACTT TCAGAAGAAC TTTGTCTGTC TGGAGAACTG CTCGTTGCAA   480
GAGCGAACAG TGACAGGGAC TGTTAAAGTC AAAAATGTGA GTTTTGAGAA GAAAGTTCAG   540
ATCCGTATCA CTTTCGATTC TTGGAAAAAC TACACTGACG TAGACTGTGT CTATATGAAA   600
AATGTGTATG GTGGCACAGA TAGTGATACC TTCTCATTTG CCATTGACTT ACCCCCTGTC   660
ATTCCAACTG AGCAGAAAAT TGAGTTCTGC ATTTCTTACC ATGCTAATGG GCAAGTCTTT   720
TGGGACAACA ATGATGGTCA GAATTATAGA ATTGTTCATG TTCAATGGAA GCCTGATGGG   780
GTGCAGACAC AGATGGCACC CCAGGACTGT GCATTCCACC AGACGTCTCC TAAGACAGAG   840
TTAGAGTCAA CAATCTTTGG CAGTCCGAGG CTGGCTAGTG GCTCTTCCC  AGAGTGGCAG   900
AGCTGGGGGA GAATGGAGAA CTTGGCCTCT TATCGATGA                         939
```

-continued (2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CGAGGATCCT TGTCTTCTCT GCAGATG                        27

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GCTGGTACCT GAATGAGCCA AGCAAATCCT C                  31

(2) INFORMATION FOR SEQ ID NO: 9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CCGGTCGACC GG                                      12

(2) INFORMATION FOR SEQ ID NO: 10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GCAGAGAAGA CAAAACCAC                               19

PROTEIN TARGETING TO GLYCOGEN

This application is a 371 of Application No. PCT/US97/14142 filed Aug. 22, 1997, which claims benefit of provisional application 60/025,107 filed Aug. 30, 1996.

FIELD OF THE INVENTION

This invention relates to isolated murine and human genomic and cDNA molecules that encode for a protein called the Protein Targeting to Glycogen (PTG) protein. This invention also relates to the PTG protein and to methods of increasing the amount of glycogen in a cell.

BACKGROUND OF THE INVENTION

While much emphasis in recent years has been focused on the identification and dissection of signaling pathways mediated by protein kinase cascades, it has long been recognized that protein dephosphorylation plays an essential role in regulating the activity of many enzymes involved in cell growth and metabolism (Krebs E. G. and Fischer E. H., *Biochim. Biophys. Acta*, 1953;20:150; Shenolikar S.,*Annu. Rev. Cell Biol.*, 1994;10:55; Saltiel A. R., *FASEB J.*, 1994;8:1034). Studies in evolutionarily distant organisms have demonstrated a critical role for type 1 protein phosphatase (PP1) action in modulating a wide variety of intracellular processes. In yeast, PP1 has been shown regulate cell cycle progression (Hisamoto N., et al., *Mol. Cell. Biol.* 1994; 14:3158; Zang S., et al., *Mol. Cell. Biol.*, 1995;15:2037), chromosome segregation (Francisco L., et al., *Mol. Cell. Biol.*, 1994;14:4731), protein synthesis (Wek R. C., et al., *Mol. Cell. Biol.*, 1992;12:5700), and glycogen metabolism (Cannon J. F., et al., *Genetics*, 1994;136:485). In mammalian cells, PP1 also has multiple physiological roles, such as regulation of glycogen metabolism (Bollen M. and Stalmans W., *Crit. Rev. Biochem. Mol. Bio.*, 1992;27:227), protein synthesis (Cohen P., *Ann. Rev. Biochem.*, 1989;58, 453), and muscle contraction (Shenolikar S.,*Annu. Rev. Cell Biol.*, 1994;10:55). Many of the metabolic effects of insulin are thought to occur via activation of PP1 (Saltiel A. R.,*Am. J. Physiol.*, 1996;33:E375). Indeed, many of the rate-limiting enzymes involved in glucose and lipid metabolism, such as glycogen synthase, hormone sensitive lipase, and pyruvate dehydrogenase are regulated by dephosphorylation. Thus, these dephosphorylations are likely to be critical to many of the metabolic effects of insulin, including stimulation of glycogen and lipid synthesis, and inhibition of lipolysis. Given the array of physiological processes presumed to be mediated by PP1, it becomes apparent that organisms must have evolved a mechanism of regulating PP1 activity to maintain substrate specificity and ensure against accidental activation of competing signaling pathways.

Early biochemical studies on the regulation of protein phosphatases lead to the hypothesis that protein phosphatases acted to constitutively oppose the action of specific protein kinases, since purified phosphatases could act on a wide variety of phosphorylated substrates in vitro. This idea has been challenged recently by the identification of tissue specific proteins that act to target Ser/Thr phosphatases to specific subcellular locations, thereby endowing phosphatases with a high degree of specificity in vivo (Hubbard M. J. and Cohen P., *Trends Biochem. Sci.*, 1993;18:172; Mochly-Rosen D., *Science*, 1995;268:247). For example, in striated muscle, two targeting subunits M and G, direct the catalytic subunit of PP1, PP1C, to different subcellular locations. The M subunit directs PP1C to myofibrils, acting to facilitate dephosphorylation of myosin (Dent P., et al., *Eur. J. Biochem.*, 1992;210:1037), whereas the G subunit localizes PP1C to both the glycogen particle and the membranes of the sarcoplasmic reticulum, where glycogen metabolizing enzymes and SR proteins serve as substrates for PP1C (Stralfors P., et al., *Eur. J. Biochem.*, 1985;149:295; Hubbard M. J. and Cohen P., *Eur. J. Biochem.*, 1989;186:71 1; Hubbard M. J. and Cohen P., *Eur. J. Biochem.*, 1990;189:243; Macdougall L. K., et al., *Eur. J. Biochem.*, 1991;196:725). In addition, PP1C is also known to interact with proteins in nuclei, an inhibitor protein, NIPP1 (Beullins M., et al.,*J. Biol. Chem.*, 1992;267:16538), and the *Saccharomyces cerevisiae* protein sds22+ (Stone E. M., et al., *Curr. Biol.*, 1993;3:13). PP1C has also been shown to interact with the product of the tumor suppressor gene, Rb, implicating PP1C in the control of tumorigenesis and cell cycle progression (Durfee T., et al., *Genes Dev.*, 1993;7:555). Thus, the targeting of PP1C to discrete subcellular locations by physically interacting proteins allows for a high degree of substrate specificity and tight control of phosphatase activity.

Recently, a number of proteins that direct PP1C to the glycogen pellet have been characterized and cloned from mammals and yeast. In *Saccharomyces cerevisiae*, the product of the GAC1 gene is required for glycogen metabolism and physically interacts with PP1C (Stuart J. S., et al., *Mol. Cell. Biol.*, 1994;14:896). In mammals, two tissue specific glycogen localizing subunits of PP1C have been identified. RG1, the glycogen binding subunit of skeletal muscle, encodes a protein product of 160 kD and is expressed in both heart and skeletal muscle (Tang P. M., et al., *J. Biol. Chem.*, 1991;266:15782). Reversible phosphorylation on two closely spaced serine residues contained within the amino terminal portion of RG1 (sites 1 and 2) has been implicated in regulating PP1C activity in response to hormonal stimulation (Dent P., et al., *Nature*, 1990;348:302). According to this hypothesis, phosphorylation of site 1 following insulin stimulation leads to a higher affinity of PP1C for RG1, leading to activation of glycogen metabolizing enzymes by dephosphorylation, while phosphorylation of site 2 by cAMP activated protein kinase A (PKA) causes a reduced affinity and subsequent release of PP1 C from the glycogen pellet. A glycogen binding subunit expressed exclusively in liver, $G_L$, was recently cloned and was found to encode a predicted protein product of only 33 kD. $G_L$ was shown to also differ from RG1 with respect to enzymatic activity towards various substrates and in the ability of $G_L$ to serve as a substrate for PKA (Doherty M. J., et al., *FEBS Lett.*, 1995;375:294).

In an effort to identify novel PP1C localizing subunits involved in regulating insulin stimulated metabolic pathways, a 3T3-L1 adipocyte cDNA 2-hybrid library was screened for PP1C interacting proteins. We describe the isolation and characterization of a novel glycogen binding subunit of PP1C, called PTG, that may act as a scaffold for the localization of critical enzymes in glycogen metabolism, including phosphorylase b, glycogen synthase, and phosphorylase kinase. PTG is expressed predominantly in insulin-sensitive tissues and was found to mediate the hormonal control of glycogen accumulation in intact cells.

BRIEF DESCRIPTION OF THE DRAWINGS

FIG. 1 shows the sequence comparison of PTG with glycogen localizing subunits of PP1C.

FIGS. 2A–D shows PP1C binding and glycogen localizing activity of PTG protein.

FIGS. 4A–D shows the binding of phosphorylase a, glycogen synthase, and phosphorylase kinase to PTG.

FIG. 5 shows glycogen synthesis in CHO-IR cells overexpressing PTG.

SUMMARY OF THE INVENTION

Figure 2A:
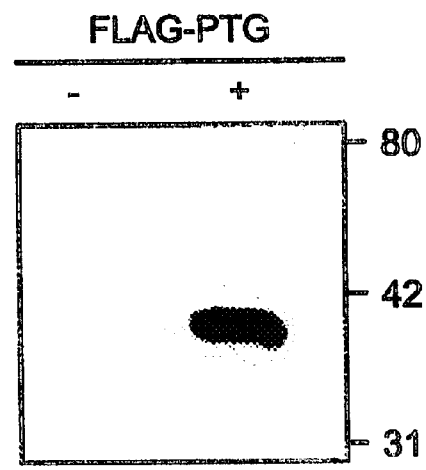

The present invention provides an isolated murine protein comprising the amino acid sequence:

Met Ala Met Arg Ile Cys Leu Ala His Ser Pro Pro Leu Lys Ser Phe Leu Gly Pro Tyr Asn Gly Phe Gln Arg Arg Asn Phe Val Asn Lys Leu Lys Pro Leu Lys Pro Cys Leu Ser Val Lys Gln Glu Ala Lys Ser Gln Ser Glu Trp Lys Ser Pro His Asn Gln Ala Lys Lys Arg Val Val Phe Ala Asp Ser Lys Gly Leu Ser Leu Thr Ala Ile His Val Phe Ser Asp Leu Pro Glu Glu Pro Ala Trp Asp Leu Gln Phe Asp Leu Leu Asp Leu Asn Asp Ile Ser Ser Ser Leu Lys Leu His Glu Glu Lys Asn Leu Val Phe Asp Phe Pro Gln Pro Ser Thr Asp Tyr Leu Ser Phe Arg Asp Arg Phe Gln Lys Asn Phe Val Cys Leu Glu Asn Cys Ser Leu Glu Asp Arg Thr Val Thr Gly Thr Val Lys Val Lys Asn Val Ser Phe Glu Lys Lys Val Gln Val Arg Ile Thr Phe Asp Thr Trp Lys Thr Tyr Thr Asp Val Asp Cys Val Tyr Met Lys Asn Val Tyr Ser Ser Ser Asp Ser Asp Thr Phe Ser Phe Ala Ile Asp Leu Pro Arg Val Ile Pro Thr Glu Glu Lys Ile Glu Phe Cys Ile Ser Tyr His Ala Asn Gly Arg Ile Phe Trp Asp Asn Asn Glu Gly Gln Asn Tyr Arg Ile Val His Val Gln Trp Lys Pro Asp Gly Val Gln Thr Gln Val Ala Pro Lys Asp Cys Ala Phe Gln Gln Gly Pro Pro Lys Thr Glu Ile Glu Pro Thr Val Phe Gly Ser Pro Arg Leu Ala Ser Gly Leu Phe Pro Glu Trp Gln Ser Trp Gly Arg Val Glu Asn Leu Thr Ser Tyr Arg. (SEQ ID NO.: 2)

The present invention also provides an isolated human protein protein comprising the amino acid sequence;

Met Ile Gln Val Leu Asp Pro Arg Pro Leu Thr Ser Ser Val Met Pro Val Asp Val Ala Met Arg Leu Cys Leu Ala His Ser Pro Pro Val Lys Ser Phe Leu Gly Pro Tyr Asp Glu Phe Gln Arg Arg His Phe Val Asn Lys Leu Lys Pro Leu Lys Ser Cys Leu Asn Ile Lys His Lys Ala Lys Ser Gln Asn Asp Trp Lys Cys Ser His Asn Gln Ala Lys Lys Arg Val Val Phe Ala Asp Ser Lys Gly Leu Ser Leu Thr Ala Ile His Val Phe Ser Asp Leu Pro Glu Glu Pro Ala Trp Asp Leu Gln Phe Asp Leu Leu Asp Leu Asn Asp Ile Ser Ser Ala Leu Lys His His Glu Glu Lys Asn Leu Ile Leu Asp Phe Pro Gln Pro Ser Thr Asp Tyr Leu Ser Phe Arg Ser His Phe Gln Lys Asn Phe Val Cys Leu Glu Asn Cys Ser Leu Gln Glu Arg Thr Val Thr Gly Thr Val Lys Val Lys Asn Val Ser Phe Glu Lys Lys Val Gln Ile Arg Ile Thr Phe Asp Ser Trp Lys Asn Tyr Thr Asp Val Asp Cys Val Tyr Met Lys Asn Val Tyr Gly Gly Thr Asp Ser Asp Thr Phe Ser Phe Ala Ile Asp Leu Pro Pro Val Ile Pro Thr Glu Gln Lys Ile Glu Phe Cys Ile Ser Tyr His Ala Asn Gly Gln Val Phe Trp Asp Asn Asn Asp Gly Gln Asn Tyr Arg Ile Val His Val Gln Trp Lys Pro Asp Gly Val Gln Thr Gln Met Ala Pro Gln Asp Cys Ala Phe His Gln Thr Ser Pro Lys Thr Glu Leu Glu Ser Thr Ile Phe Gly Ser Pro Arg Leu Ala Ser Gly Leu Phe Pro Glu Trp Gln Ser Trp Gly Arg Met Gln Asn Leu Ala Ser Tyr Arg. (SEQ ID NO.: 4)

The present invention also provides an isolated murine genomnic DNA molecule comprising the sequence:

GGATCCCGCTGGCCCAGGGCTCAGG-
GACTCTACGGCCGCCTTCC AGCACGCTCTGGTCA-
CATCCAGCCCCGCGGTGATCACGTTCAG
GGGCAGGGGCTCGTGCCCCAGCTGCA-
CAGTGGTTGGTCAGGGC GCACGGCCTTTGATTG-
GTCGGAGGGACCGGTTCACGTGATCTGG
CTTTGATAAGCTGCCTCCCGGTTGCCT-
GCGGTCAGTCGGCCGGC TGGACCGCGGCGCTG-
CATCCTCTTAAGTACTGAGTGCGAAGTTG
CTCAGGGTGCGGTTGTCGCGGTCGC-
CGCTGCCTCTCGGTCCAAT GAACTGCACCAGG-
TAAGTTCAGTGCAACTCTGCGCCCGAATGG AGGG-
GAGCCTGCAGCTGCOGGGACTTGGGGGCTTTTGT
GGTTTT GTCTTCTCTGCAGATGGGAGACTCCCAG-
GTTGATGGCTGAGTTG AATCGTCCCGGAGGCTTG-
GAAGGGATGGAATTTGAGTTGAATTT CTTAGGCGC-
CTGTTTTGGGGAATCTAACATCTCAACAGTAGAAA
CTGCCTTAGTGAGTCAGTTTTAGCTGG-
GATTCCTTTGCTGAAGT GACTCTGTTGC-
CTTTGAGCTCAAAGACCCAAAAAATTGGGTTGC
AGCTTAGTTTTATTGATGAGGTAGTT-
TAGCCTGTGGCAAAAGGT AGAGGATTTTG-
CATTTCTTCTTTCCCCACTTCCCCTCTCCTGGTT
TTGTCATAAAAAAATGCAGTCTTA-
GAGTTTGAGCAAGCTATTAT TTTTAACTCCTGGC-
CAGGACTTAGGAATTCCAGGGAAATAGCCC ACT-
ACTAAAACTTTCTATAAATGCAGGAGTAAAAAAG
GAAAAA AACCAAAAAAACTAAAACAAAAA-
GAAAAACAAGAACAGCTCA ACCAATAAAAAAC-
GAACAACAGCTCCATCAACCAGGCAACCAA GAC-
CATCTCACGAAATGTTGCATCTCCAGTTGTAACTT
AGTCCA AGAATTCTCCCTCCCCAAATCCTGC-
CTCTTAATGGTTGTGAGAC AAATAGACTTTGAG-
GTTTTGTTGCTGGAAGTTTGTAATCCTCTCA
GAAAAACCCTAGAGCTATTAAAGTGAGT-
TCAGTATACATTCTTT ACAGGCCACTTTGTGATGAT-
GACCATATACAGGGTGCTGTGCTT AGCACTGGTAT-
GAAGAGAATTCTTCAAGCCAGACTATATTTATG
ATCAAAATATGTTATATA-
CATATATAAACTGTTAAAGAATAAAT AAT-
TAATAAAGCCCCAGACTCCAAAATG-
GCACCTACTGTATTTC
ATGTTTCTTTGATTTATAAGGCTGACAT-
TGGAGAGGAAAAACCT AATTCTGTAAGTGTG-
GAATTATAGTGTGGTTCAAGGGAAAGAA AGGCCA-
GAAAAGTCTTGATGGATGGTTCTTTGTTTGATGCA
AAC TATTGTTATTGCCTTCCTACTTGTAAAT-
AGGACCTGCTCAACAAC AGGAAACATCATA-
GAAGCCCAAACCAGTAGATGCTATAATNCC
ATCAGTCAAAGATAATGAACATCTTAGT-
GTTTNCCTTTGTAGTTT NCAGTATTTATAAAT-
NCATATATCTUCAGTGTATTTAAAACAG CTCATTT-
NCTGGTTATCAGTTTTTAAAACTACTTTATGTTGT
GTA TATATAATGTACACTGCAGGCTACAAGA-
CAGAGCTATAGTAAA GTGGTTATTACTGGTCA-
GAATGAACAANTCTGTTATCCCTGCAG GTTAGC-
TATTCCCTTTATAGTTGGACCTGTCATGGGCATCT
TTCC TATATGAACTGTCAGATTGTT-
TAAAGTTTTTCCTTTAGTCTGTGA GATGTTGGCTG-
GTGTTGCAGTTGGTCATTTGTGAAAtGATGAGG
ATGACTGTGATAAAATGAAAAAGTCAT-
TCTTTCTTTTAACAAGC GTCACCTACTGT-
CACTCTAAGGACAGCATGACATTTTAAGAATT GCT-
TCATTTATTGTTTCCCAAGTGGATTACTTCTCCTGA
GAAGTAAAACCGGTTCGAGAGCCAAAATAGGAAA-
CAGCAGCCAGAGGG AGCGAGAGGCTGGGACTGT-
GATAATGGAAGAAGCTGTCTGGCC AATG-
GACTCTTTTGGGGGAAGCTTTAAGAACATATTTA
CCTTTC TGGCTCCATGCCATGAAGCTCTACTG-
TAGTGGTTTTAAGTCCCC GGAATCT-
GAATTTTTTTTTCTAAAGGAAA-
GAAACTTCTCAGGT
CTTGTTGATCTGACAGGTTTAAGAAC-
CACTGGCCCAGAACAGAG TACATAATTCCAA-

GAGCTGTGTCAGACTTGTTCAGATAGAGCCC TCT-
TGTTTCTCAGATGGAGAAACTGAATCCTCTCTGAG
TGTTTCA GGCAGTTTACACATGGGCCCAGCAGCCT-
GCCAAGCACAGAGCT AGACTGTAGATCTCATCAC-
CCCAGTGCTCTCCTTTTCTCCACGTG ATAGCAC-
CTCTCTGCACTGGAGTACTAGTGTGTGTGCATTT
GGG ACCAGGGGAAGACGACTCCAGACCTCG-
GTGATTACCACTGTTTT TTTTTTTTTTTCTCATTC-
CAGAATGATCCATGTGCTAGATCCAC GTCCTTTGA-
CAAGTTCCGTCATGCCCGTGGACATGGCCATGAGG
ATTTGCTTGGCTCATTCACCACCTCT-
GAAGAGTTTCCTGGGTCCT TACAATGGTTTTCAAC-
GAAGAAATTTTGTGAATAAATTGAAACC
TTTGAAACCATGTCTCAGTGTCAAGCAG-
GAAGCCAAATCGCAG AGTGAGTGGAAGAGCCCA-
CACAACCAAGCCAAGAAGCGGGTCG TGTTFGCG-
GACTCCAAGGGGCTGTCACTCACTGCTATCCATGTC
TTCTCCGACCTTCCAGAAGAAC-
CAGCGTGGGACCTGCAGTTTGA TCTCTTGGACCT-
TAACGATATCTCCTCCAGCTTAAAACTTCACG
AGGAGAAAATTGGTFTTTGATTTTC-
CCCAGCCCTCAACCGAC TACTTAAGTTTCCGG-
GACCGCTTTCAGAAGAACTTTGTCTGCCT
CGAGAACTGCTCTTTGGAAGATCGGACG-
GTGACCGGGACAGTG AAAGTGAAGAATGT-
GAGCTTTGAAGAAGGTTCAGGTCCGGA TCAC-
CTTTGACACCTGGAAAACCTACACAGATGTGGAC
TGTGTC TACATGAAGAATGTTTACAGCAGCTCA-
GACAGCGACACCTTCTC CTTTGCAATCGACTTGC-
CCCGTGTCATTCCAACTGAGGAGAAAA TTGAGT-
TCTGCATTTCTTATCACGCTAATGGGAGGATCTTC
TGG GACAACAATGAGGGTCAGAATTACA-
GAATTGTCCATGTGCAAT GGAAACCTGACGGAGT-
GCAGACTCAGGTGGCACCCAAAGACTG TGCATTC-
CAACAGGOGCCCCCTAAGACTGAGATAGAGCCC
ACA GTCTTTGGCAGTCCAAGGCTTGCTAGCG-
GCCTCTTCCCAGAGTG GCAGAGCTGGGG-
GAGAGTGGAGAACTTGACCTCCTATCGATGA. (SEQ
ID NO.: 1)

The present invention also provides an isolated human genomic DNA molecule comprising the sequence:
CTTGACCTGTCTAAGCTTTCAGTTCCT-
CATCTGTGAAATAAAGA GTTTGATGCCTATCAC-
CTCCTACCTCCATAATTCTAACCATTGATGGGT CAT-
TAAAATAAGACAATATGGTGCAGCGGTTATTGCTC
TGGTATCAGC CAGGCTCTAATCCCTGCTCTACCT-
GTGAGAACCTGGGCAGGTTTTTTT
TTGTTTTTGTTTCGAGATA-
GAGTCTCGCTCTGTTGCCCAGGCTGGAG
TGCAGTGGTGCAATCTCAGCTCACTG-
CAACCTCCGCCTCCCGGGTTCA AGCGATTCTCCT-
GCCTCAGCCTCCAGAGTAGCTGAGAGTA-
CAGGTGTG
CACCACCATGCCCGGCTAATTTTTG-
TATTTTTAGTAGAGATAGGGTTTC ACCATGTTGGC-
CAGGCTGGTCTTGAACTCCTGGCCT-
CAAGTGATCCACT
GGGCAGATTTCCTGACCATTCAGT-
GTCTCCGTTTTCTTTTCTCTAAAAT GGGAT-
TAATAACTGGACATATCACATAGGGT-
TGTTGTGAGGATTGAAT
TGATAGCACATAGTGTTTGGCACAGAG-
TAAAGGCTCAACAAGCAGCAG CTATTCT-
CAATATTTTAGCTCAGGCACCAGGCGC-
CTTGAGGTGATAGA
GTAAAAACTCTAGCTGAGAGATCAAGTA-
GAAACTTGGGAACTAGCCCG GGTGGAACACAG-
GCACTGGGCATCGTGCTGAGTCTGT-
TCATTGGCACC
ATCTTACTTCATCTTCAGAACGTTAC-
TATCTCTGTTTTACACATGAGGA AACTGAGGTTA-
GAACTTGCCTAGTTCGGTAGCTAG-
TAAGTGTCAATCC
AAAGACCTTCCAGCTAGTTTTGGT-
TGAGCTAAAGGGGCTAGAAGACCT GCCATTAGT-
TAGATATTTCATTTCAAAAATAAAAC-
CCAGGCATGAAGT
CCCTTTCCCAGTGATATTCAGTGT-
GATTTTTTTCTTCACTCTAATAATTT TAACAATTC-
CACTGTTTGACAGTTGTTTAAAAGACAT-
AGGAATTTTGT
ATATTTTAATTGACTAATGGATAGCT-
CAATTAGGGGAGCAAAACTAGG ATGTGGGTTT-
TATAAAAATAATTTAGACTTGACTTAGA-
CATTTAATTTT
ACAGTTGTAAATGATGGTCTAAAAAT-
TCTTCAAACTAATCAAAATAAT GAAACTTCAGC-
GAAAGTGAGTGGCTCAGAAGGCCCAT-
GAAACATACG
GCGTGATTTTTAAATTTTATTTTAA-
CATTTTGATTTCCACACCACTGCC AAAGGACGTCA-
GAATTGAGTAAGGGGTTTGGGTTGACT-
GCTGCCTCTT
GACCGGCTGTATGTGTGAAAAGGGT-
CATTTCACTTCCGGCTTTAGTGTT CCCCGCAGGG-
GAGAAAATTGAAGAATAGACAGAAATAC-
GAAGTGTCT
TTTAATTAAATGCCACCTTGGTGTIT-
TATGGGGCTCGTATGCTTTCCTA ACAACATTTGTTA-
GATAAGTTGGTAATTCCCGGCAGCTGTCTACTGTGT
GGTGCATCTGTGAACTCATACTAATC-
GAAAAGCATGCAGCCAGTTTGG GATCGCGCAG-
GCTAAGGTGAGGGAGAAATGCGGATA-
CACCGGGTAAT
GAACGATATAAACATTTCAAATGCGATA-
CACATTCGGTTTGAGCCACA TCTTCTGTGTGCA-
GATTCACCCGCAGTGACCCACAAAGCTATTCCCAA
GTAACAGCCGCCCCAAGCCTGAG-
GCACTGGCGCCCCGCCTGGGCGAG GCTGGCT-
GCGCTCTCTCTTGGCCGGCGCCCGCTG-
CATGCGGTACGTGCC
TGCCCGGCCCCTAGCCCA&GGTTCCCGTTACGCG
GCTGGTTCCAGCTG GCCGCGGAGTCCCAGAAC-
CTCCCCGGGATGCCCAGATAGCTCTCTGCA
CGTCTGGCCCCGGGGCGATCACGTTGC-
CGGGGCGAGGGCTGGCGCCCC AGCTGGGCGCTG-
GTTGGTCGCGCCCTGGGGCTCGAGGC-
CCGGCGATTG
GTCCCAGGGATCGGGTCACGTGCTTGG-
GAGCAGATAAGCGGCCTCTAG GCGCCGGGCCCT-
CAGTCTCTCCCAGCGACCGC-
CGCGGGGGCAAGGCCT
GGAGCTGTGGTTCGAATTTGTGCAG-
GCAGCGGGTGCTGGCTTTAGGG TCCGCCGC-
CTCTCTGCCTAATGAGCTGCACCAGG-
TAGGTTCGCTGCAA
CTCTGCGCGCTAGGAACACAGGG-
GAACGCGCAGCTGTGGGGAAGTTG
GGGGGCGTTTCAGTTCTATCATCTCTG-
GAAATGGACACCCCAGGGGGA GGACAAGTG-
GACTGACTGCGTAGTTGAATCTGGCAAC-
CGAGAGGCCTT
GGAGGTGTAGAAATTTGGCTCTATTTCT-
TAAGCAGAGCCTATTTTAGTA ATCAGCATCT-
FAAAGCAGAAATTATCTTAACGTGAAT- CAGCTTGAGTT
AGGATTTTCTCATGGATGCGGCTGT-
TCTTTTGGTCCTGCACAAATGTCC CAAA-
GACTCGGGCAGCTGAAGTGGTGAGAA-
CAGCACTCTGACATTGCT
GGTTAGGTGGTTTAGCTTGGAG-
GAAAAAAATTACAGGACGACGTTTGC ATTCAT-
TCGTCCTTCTTATCACAGTTTGCCATAG-
CAAAATCTCAAGAGT
TTGAGCAAACGATTACTTTTAACTCT-
TGTCCAGGACTTAAAGTTCCAAG GAAATCAC-
CCAAACTAAAACTGTCTTTCTATAAATG-
CAAAAAGTAAAA
AAAAAAAAACAAAAAAACCAAAAAAAAC-
CTCCCATAAAACTACTTTA AATAGCTTCTCCAGA-
CATAGCTTAGCAGAAGANTTCTCTAAAAATCCT
GCCTATTAACTATTATTAGACCCA-
CAAATATAGCTTTAGCTTTCATTTG TTTGTT-
NTAAGTTTGCAGATCTCCCAGAAAAAC-
CCAGAGCTAACACA
GTAAATTCTGCGAGTGTTATTACA-
CACTTTTGTGATAATGACCACTTGC ATACATGTTTA-
GAGCTGCTGTGAGGAGAGTTACTAAAGC-
CAGACTGAG
AAATGTCGTGTACAGTATACACAC-
CTCTTACTTGTAAGGCTAAGAT AGG-
GAAAAAAATCTTAATACCATAAGCTTG-
GAAATATATGATGAGGGC
TAAAGGTCAGAGAAAGTCTTCTTTATA-
GATGCTTCTTGGTTTAATATT GCTGAGCATAGTCAT-
GTTTAAAACTTTAAATGGTTTTATTGTCTTTCTA
CTTATAAATGTCTATTAGAAAATGC-
CAAAAAAGAACAAAAACGAAAA TAGATAATC-
TATAATCCTATCACCCAGAAATAATAAT-
TATTAAATTATT
AGGAAAGGTGTATTTCCTATA-
GAGTTTTTCAATATTTATAAGTTTGTAT ATATAAAAT-
GTATATTTTAAAACACTCCAACTTTCAG-
GTAATCAGTTTT
TCCACTTAAATGTGGACTTGT-
CATGGGCATCTCTTTAGGTGAATTATCA ATTATAT-
AGTTTTTAAGTGCATATGAATTGTTG-
GCTTGTATTTCAGTGG
TTATTTGTGAAAAATAAGAGCAT-
GATAATCAAAGTGCAAAGATGATTC TTTGACTTCT-
TCTCTAGCCTTCTCACTTTCAAAACTG-
CATGTTATTTTT
TTTTTCAAGTGAATTACCTTACCA-
GAGAAGTGTCAATCAATTFAGCAGC AAAATAAGC-
CAACGTAGCCAGAGGGAGCA-
GAGGGTCTGGAACTGTGG
CTCCTGAACCTGTCTGGTCATTAGAAT-
CACCTGGGAAGCTTTAAGAAC ATACCCATCCCTTG-
GCCCTAGCCCCAGAAGTTCTGCCTCAGTAGTTCTG
AGTCCCAGGAATTGGAAAGAAAGAA-
GAAAGAGAAAGAGAGAGAGAG AGGAAGAAAG-
GAAGGAAGGAGGGAAGGAGGAAAQGAG-
GAAAGACAA
GAAAGAAAGAAAATGAATTCCCTAGA-
CATAGTGACCAGACAGGTTTG AGGACCACTGGTC-
CAGAACAGAGCACACAGTTCTCAAGGCT-
GCCTTGG
AGATAATCAAATCGAACCCTTT-
TATTTCTCAGATGGGGAAACTGAGAC CCCCATCAC-
CCTCTAAGTGTTTTAAGCAATTAATAGC-
CTTTACCGGCCA
AGGGTAGAGGTAGACATAGAAGATCT-
GATCACTTAATACTGTTCTCTT TTACTACATATGAT-
AGCACCTGCCTGATATCTAGTGCACTGGCTATAAT
TCAGTCAGCACAAAAATAGTACATATG-
TATTTGGCACTGGGGAAGAGC ATTTCCGATCCAG-
GTGATAATCCCTCTTCTTTTTGCATTCCAGAATGAT
CCAGGTTTTAGATCCACGTCCTTTGA-
CAAGTTCGGTCATGCCCGTGGAT GTGGCCATGAG-
GCTITGCTTGGCACATTCACCACCTGT-
GAAGAGTTTCC
TGGGCCCGTACGATGAATTTCAACGAC-
GACATTTTGTGAATAAATTAA AGCCCCTGAAAT-
CATGTCTCAATATAAAACACAAAGC-
CAAATCACAGA
ATGACTGGAAGTGCTCACACAACCAAGC-
CAAGAAGCGCGTTGTGTTTG CTGACTCCAAOGGC-
CTCTCTCTCACTGCGATCCATGTCTTCTCCGACCT
CCCAGAAGAACCAGCGTGGGATCTG-
CAGTTTGATCTCTTGGACCTTAA TGATATCTCCTCT-
GCCTTAAAACACCACGAGGAGAAAAACTTGATTTT
AGATTTCCCTCAGCCTTCAACCGAT-
TACTTAAGTTTCCGGAGCCACTTT CAGAA-
GAACTTTGTCTGTCTGGAGAACT-
GCTCGTTGCAAGAGCGAACA
GTGACAGGGACTGTTAAAGTCAAAAAT-
GTGAGTTTGAGAAGAAAGTT CAGATCCGTAT-
CACTTTCGATTCTTGGAAAAACTACACT-
GACGTAGAC
TGTGTCTATATGAAAAATGTGTATGGTG-
GCACAGATAGTGATACCTTCT CATTTGCCATTGACT-
TACCCCCTGTCATTCCAACTGAGCAGAAAATTGA
GTTCTGCATTTCTTACCAT-
GCTAATGGGCAAGTCTTTTGGGACAACAAT GATG-
GTCAGAATTATAGAATTGTTCATGT-
TCAATGGAAGCCTGATGGG
GTGCAGACACAGATGGCACCCCAGGACT-
GTGCATTCCACCAGACGTCT CCTAAGACAGAGT-
TAGAGTCAACAATCTTTGGCAGTCCGAGGCTGGCT
AGTGGGCTCTTCCCAGAGTGGCA-
GAGCTGGGGGAGAATGGAGAACTT GGCCTCT-
TATCGATGAATTAAGCAACAATG-
TAACTGGTCTTGACTTGTC
ATATTCCCCCATGCAATCCTAGGTCTG-
TATTGCTCAATTTTAGGAAGCC TTTGCTACTCCAT-
CAGTAGGTTTAGATTTGAGCTTTTGAAACCTGGCTA
TGGAAAAGAAAGACACTTGAGAATTTAT-
GTTGGGGTCTGTACAGATAA ATGCTAAC-
CCAATTTGGCTTTGAAGGATCAAGTAA-
CAGGTTGAAAACT
ATTTTTATAAAGGTAATACTTTTTCAGT-
TCCCTTCTTCCTTCCCTCTCAA TCCAC-
TAGCTTTCATGTTGGGCAAGGAAAAGT-
TGAGGAAGGATGGCTG
ATGGTGATGGAAAGCTATGTTAATGG-
TATGAGGAATGTGTGAAAAGTA TACA-
CAAAGGGCTCTGAAGCTCAAGTCAGAG-
GAGTGGAGGGTCTGATC
ATTGTTGGTGGAAAAACGTAAGGT-
TATTTTGTGTTTTTAAGTTGGTTTT ACAATTCTTTC-
CTGGGGAAATTATTTCTOGAGGG-
GAAAAAGATCCATT
CTACGTATCCTTGTG-
GAGAAAAGCTAAATAACCTTTAAGAATGTGGGT
GGTATTGGAGAAAGAAGATGAATTAT-
AGCTCCGGAGAATCAAGATCT. (SEQ ID NO.: 3)

The present invention also provides an isolated murine cDNA molecule comprising the sequence:
ATGGCCATGAGGATTTGCTTGGCTCAT-
TCACCACCTCTGAAGAG TTTCCTGGGTCCTTA- CAATGGTTTTCAACGAAGAAATTTTGTGAATAAA
TTGAAACCTTFGAAACCATGTCTCAGT-
GTCAAGCAGGAAGCCAAATCG CAGAGTGAGTG-
GAAGAGCCCACACAACCAAGCCAA-
GAAGCGGGTCGT
GTTTGCGGACTCCAAGGGGCTGTCACT-
CACTGCTATCCATGTCTTCTCC GACCTTCCAGAA-
GAACCAGCGTGGGACCTG-
CAGTTTGATCTCTTGGAC
CTTAACGATATCTCCTCCAGCT-
FAAAACTTCACGAGGAGAAAAATTTG
GTTTTTGATTTTCCCCAGCCCTCAAC-
CGACTACTTAAGTTTCCGGOACC GCTTTCAGAA-
GAACTTTGTCTGCCTCGAGAACT-
GCTCTTTGGAAGATCC
GACGGTGACCGGGACAGTGAAAGTGAA-
GAATGTGAGCTTTGAGAAGA AGGTTCAGGTCCG-
GATCACCTTTGACACCTGGAAAACCTACACAGATG
TGGACTGTGTCTACATGAAGAATGTTTA-
CAGCAGCTCAGACAGCGACA CCTTCTCCTTTG-
CAATCGACTTGCCCCGTGTCATTC-
CAACTGAGGAGAA
AATTGAGTTCTGCATTTCTTAT-
CACGCTAATGGGAGGATCTTCTGGGAC AACAAT-
GAGGGTCAGAATTACAGAATTGTCCAT-
GTGCAATGGAAACCT
GACGGAGTGCAGACTCAGGTGGCAC-
CCAAAGACTGTGCATTCCAACA GGGGCCCCCTAA-
GACTGAGATAGAGCCCACAGTCTTTG-
GCAGTCCAACT
GCTTGCTAGCGGCCTCTTCCCAGAGTG-
GCAGAGCTGGGGGAGAGTGGA GAACTTGACCTC-
CTATCGATGA. (SEQ ID NO.: 5)

The present invention also provides an isolated human cDNA molecule comprising the sequence:
ATGATCCAGGTTTTAGATCCACGTC-
CTTTGACAAGTTCGGTCAT GCCCGTGGATGTGGC-
CATGAGGCTTTGCTTGGCACATTCACCACCTGT
GAAGAGTTTCCTGGGCCCGTACGAT-
GAATTTCAACGACGACATTTTGT GAATAAAT-
TAAAGCCCCTGAAATCATGTCT-
CAATATAAAACACAAAGC
CAAATCACAGAATGACTGGAAGTGCTCA-
CACAACCAAGCCAAGAAGC GCGTTGTGTTTGCT-
GACTCCAAGGGCCTCTCTCTCACTGCGATCCATGT
CTTCTCCGACCTCCCAGAAGAAC-
CAGCGTGGGATCTGCAGTTTGATCT CTTGGACCT-
TAATGATATCTCCTCTGCCTTAAAACAC-
CACGAGGAGAA
AAACTTGATTTTAGATTTCCCTCAGCCT-
TCAACCGATTACTTAAGTTTC CGGAGCCACTTTCA-
GAAGAACTTTGTCTGTCTGGAGAACTGCTCGTTG
CAAGAGCGAACAGTGACAGGGACTGT-
TAAAGTCAAAAATGTGAGTTTT GAGAAGAAAGT-
TCAGATCCGTATCACTTTCGATTCTTG-
GAAAAACTAC
ACTGACGTAGACTGTGTCTATAT-
GAAAAATGTGTATGGTGGCACAGAT AGTGATACCT-
TCTCATTTGCCATTGACTTACCCCCTGT-
CATTCCAACTG
AGCAGAAAATTGAGTTCTGCATTTCT-
TACCATGCTAATGGGCAAGTCTT TTGGGACAA-
CAATGATGGTCAGAATTATAGAATTGT-
TCATGTTCAATG
GAAGCCTGATGGGGTGCAGACACAGATG-
GCACCCCAGGACTGTGCATT CCACCAGACGTCTC-
CTAAGACAGAGTTAGAGTCAACAATCTTTGGCAG
TCCGAGGCTGGCTAGTGGGCTCTTCCCA-
GAGTGGCAGAGCTGGGGGAG AATGGAGAACTTG-
GCCTCTTATCGATGA. (SEQ ID NO.: 6)

DETAILED DESCRIPTION OF THE INVENTION

PTG is a PP1C binding protein with homology to known glycogen binding proteins: A 3T3-L1 adipocyte cDNA library fused to the Gal4p transcriptional activation domain was screened for proteins that could interact with a Gal4p-PP2C DNA binding domain fusion. Library plasmids containing interacting proteins were identified by the ability to induce transcription of the integrated GAL1-lacZ reporter. Of approximately $3.5 \times 10^5$ primary tranformants, 27 were positive for β-galactosidase activity. One class of interacting cDNAs, typified by clone B1-1, consistently gave the highest levels of β-galactosidase activity when plated on X-gal containing media. Induction of β-galactosidase activity was dependent upon coexpression of BD-PP1 C, since β-galactosidase activity was not observed when non-specific gene fusions were used. Partial DNA sequence from the GAL4 fusion junction followed by a BLAST search revealed that the cDNA contained in clone B1-1 was homologous to the hepatic glycogen binding subunit ($G_L$) cloned from rat liver (Doherty M. J., supra., 1995), both in nucleotide and predicted amino acid sequence. Sequencing of an additional clone (B2-2) from the same class provided a probable translational initiation site (Kozak M., *J. Cell Biol.*, 1989;108:229). The PP1C interacting cDNA contained in clones B1-1 and B2-2 has been assigned the name PTG.

Analysis of the predicted primary amino acid sequence of PTG revealed significant homology with other proteins previously shown to localize PP1 C to the glycogen particle (FIG. 1). Sequence comparison of the predicted protein product of PTG to known glycogen binding subunits of PP1 C indicates that PTG is most homologous to $G_L$ (42% Identity; 60% similarity), with less striking homology to the skeletal muscle protein RG1, and Gac1, the yeast glycogen binding subunit (Stuart J. S., supra., 1994) (26% identity; 49% similarity and 27% identity; 50% similarity, respectively). Interestingly, the residues corresponding to phosphorylation site one and two of RG1, which were implicated in hormonal control of PP1C activity (Dent P., supra., 1992), are not conserved in the predicted PTG protein.

PTG can direct PP1C localization to glycogen both in vivo and in vitro: The homology of the predicted PTG protein with $G_L$, RG1 and Gac1 suggests that PTG might bind simultaneously to both PP1C and glycogen. We tested this hypothesis directly by evaluating these associations in both in vivo and in vitro assays. A FLAG epitope tagged PTG construct (FLAG-PTG) was transiently transfected into CHO cells over-expressing the insulin receptor (CHO-IR), followed by immunoprecipitation with αFLAG antibodies and subsequent immunoblotting with αPP1C antibodies. PP1C could be co-immunoprecipitated from cell lysates with the antibodies directed against FLAG-PTG (FIG. 2A), demonstrating direct association of PP1C with PTG in vivo. This association was unaffected by treatment of cells with insulin. Moreover, PTG did not appear to undergo phosphorylation in response to insulin, and was not a substrate in vitro for cAMP-dependent protein kinase, or other protein kinases in lysates from insulin stimulated cells (not shown).

Figure 2B:
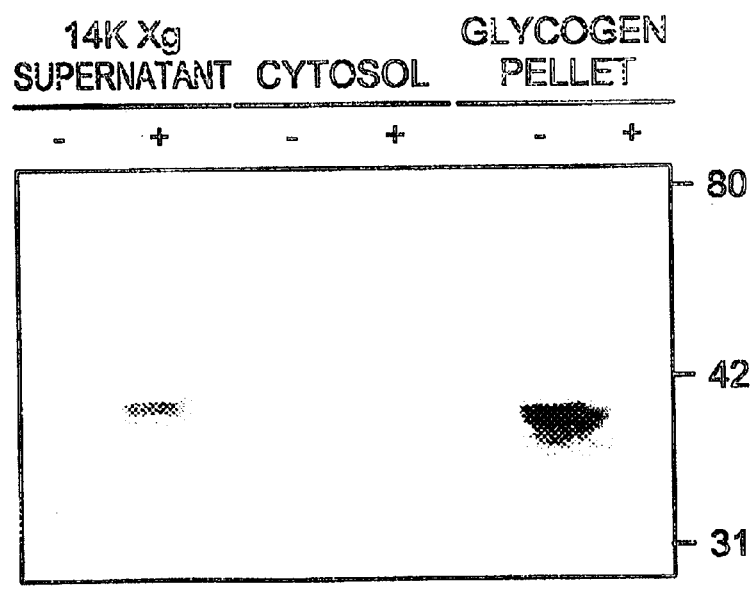
Figure 2C:
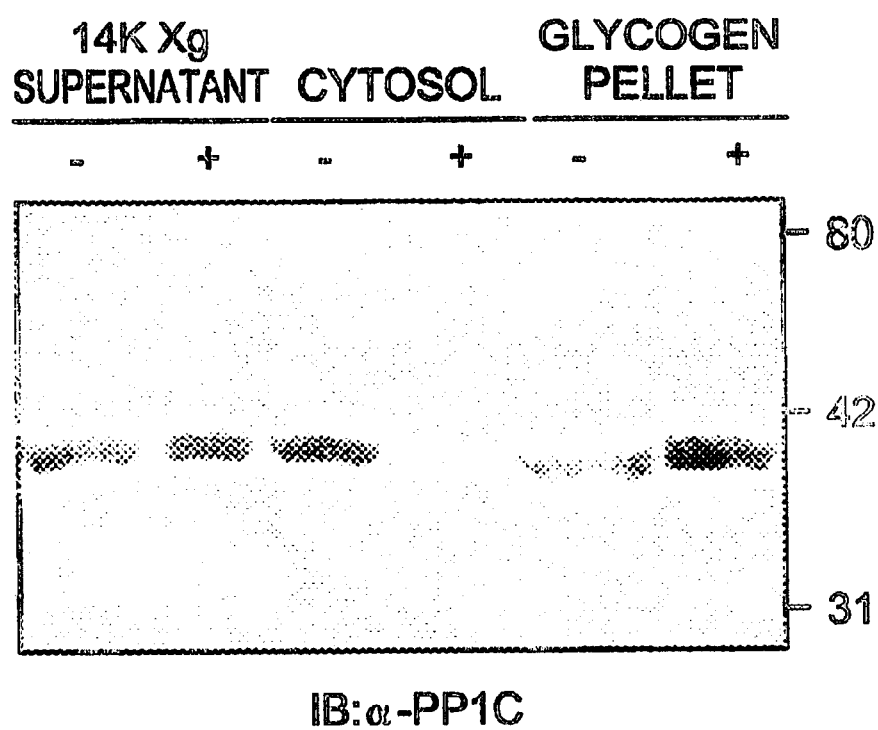

To determine the subcellular localization of PTG, similarly transfected CHO-IR cells were fractionated by differential centrifugation followed by SDS-PAGE and immunoblotting with αFLAG antibodies. FLAG-PTG in the 14K×g supernatant was found to localize exclusively to the glycogen-enriched cell fraction (FIG. 2B). Immunoblotting of these same samples with αPP1C antibodies showed that overexpression of FLAG-PTG caused a dramatic translocation of PP1C from the cytosol into the glycogen pellet (FIG. 2C). Binding of PP1C and targeting to the glycogen fraction was also observed in vitro. Addition of a GST-PTG fusion protein to 3T3-L1 adipocyte lysates caused an 8-fold increase in the PP1 activity sedimenting with the glycogen pellet, whereas the addition of a irrelevant GST fusion protein (enzymatically inactive tyrosine phosphatase PTP1B) had no effect on the localization of phosphatase activity to the glycogen pellet (FIG. 2D). These data demonstrate that PTG can simultaneously and specifically associate with both PP1C and glycogen.

Figure 3A:
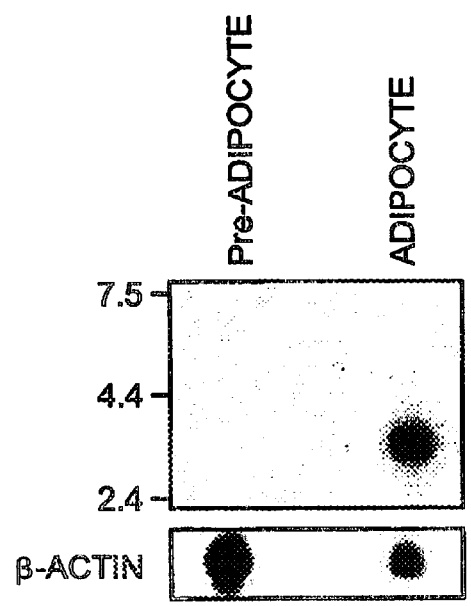
FIGS. 3A–B shows the tissue distribution of PTG expression.

PTG is expressed in insulin responsive tissues: Although many tissues and tissue culture cell lines express insulin receptors, the metabolic actions of insulin occur mainly in fat, liver, and muscle cells. Other PP1C-targeting proteins are expressed in a tissue specific manner. RG1 is expressed in muscle tissue (diaphragm, skeletal muscle, and heart) (Tang P. M., supra., 1991), whereas $G_L$ is expressed exclusively in liver tissue (Doherty M. J., supra., 1995). To determine the tissue distribution of PTG expression, a rat multi-tissue northern blot (Clontech) was hybridized with a probe prepared from the cDNA insert of clone B1-1. An mRNA of approximately 2.3 kb was detected in all tissues except testis (FIG. 3A). However, the PTG mRNA was most abundant in skeletal muscle, liver, and heart. PTG transcript was also detected in RNA prepared from rat adipose tissue (not shown).

Figure 3B:
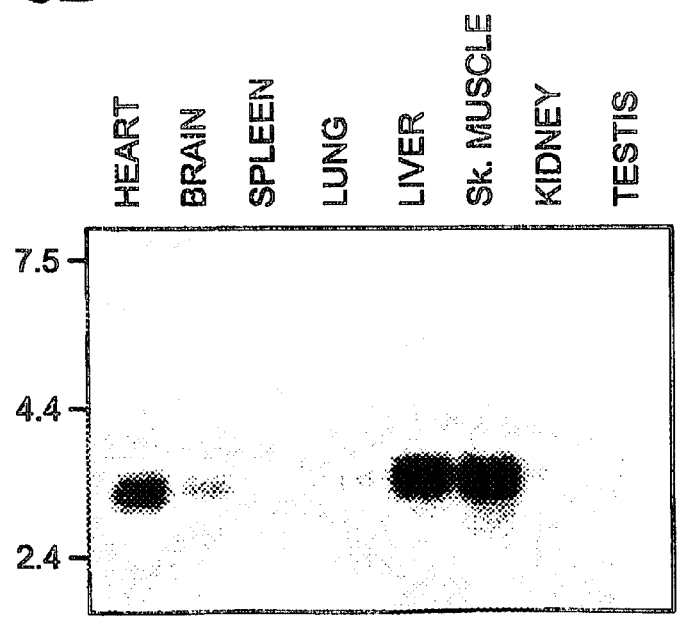

The differentiation of 3T3-L1 fibroblasts into adipocytes is correlated with a significant increase in insulin sensitivity, including the stimulation of glycogen synthesis. The expression of many genes critical to insulin action is increased during adipocyte differentiation, including the insulin receptor, GLUT4 and others (Reed B. C., et al., *Proc. Natl. Acad. Sci., USA,* 1977;74:4876; Rubin C. S., et al., *J. Biol. Chem.,* 1978;253:7570; de Herreros A. G. and Birnbaum M. J., *J. Biol. Chem.,* 1989;264:19994), although PP1C levels remain constant (Brady M., et al., in preparation). To determine if PTG expression is correlated with the observed increase in insulin sensitivity, northern analysis was performed on RNA isolated from both 3T3-L1 fibroblasts and fully differentiated adipocytes. A hybridizing mRNA species of approximately 2.5 kb was observed in 3T3-L1 adipocytes, whereas it is weakly expressed in pre-adipocytes (FIG. 3B). Thus, PTG is expressed mainly in liver, muscle, and fat tissues in which the regulation of glycogen synthesis plays an important part in insulin action. The tissue distribution of PTG is therefore significantly different from that of previously described glycogen binding subunits of PP1C (Tavy P. M., 1991 and Doherty, M. J., 1995).

Figure 4A:
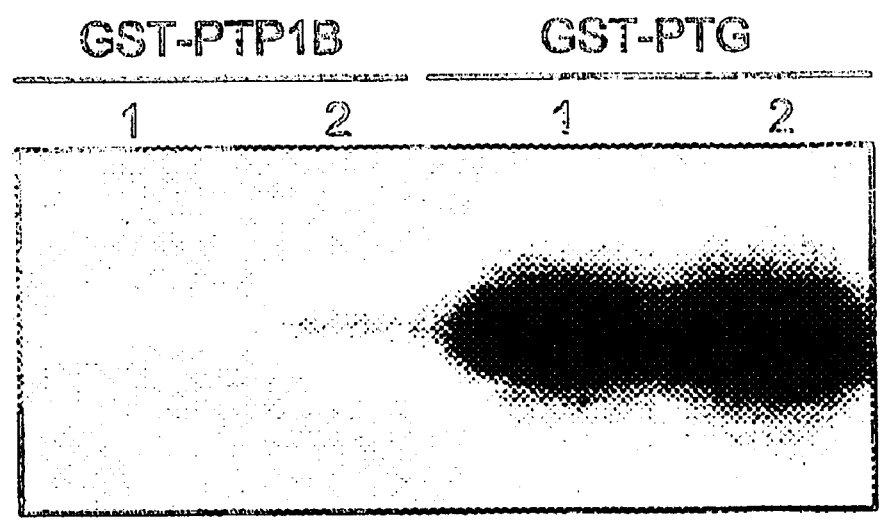

PTG can associate with multiple proteins involved in regulating glycogen metabolism: Glycogen synthesis and breakdown is regulated by the reciprocal actions of protein phosphatases and kinases. To determine whether PTG is involved in the localization of the metabolizing enzymes, and of the kinases and phosphatases involved in their regulation, a series of in vitro binding assays were performed with a bacterially expressed PTG fusion protein. First, we examined the ability of PTG to bind to phosphorylase a, the phosphorylated, active form of the enzyme that directly catalyzes glycogen breakdown. GST-PTG bound to glutathione-Sepharose beads was incubated with [$^{32}$P]-phosphorylated phosphorylase a. After extensive washing, bound proteins were analyzed by SDS-PAGE followed by autoradiography. GST-PTG efficiently bound to phosphorylase a, but did not bind an unrelated GST-fusion protein, GST-PTP1B (FIG. 4A). To determine whether PTG could also target the anabolic enzyme involved in glycogen synthesis, glutathione-Sepharose bound GST-PTG was incubated with purified glycogen synthase. Glycogen synthase activity was specifically associated with GST-PTG, and not with an irrelevent GST-fusion protein, PTP1B (FIG. 4B).

Figure 4C:
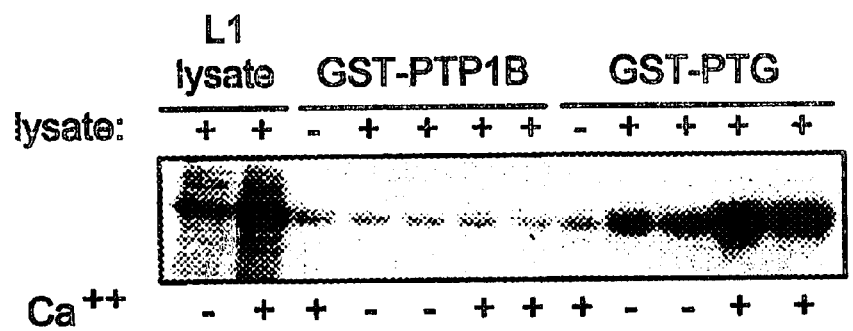
Figure 4D:
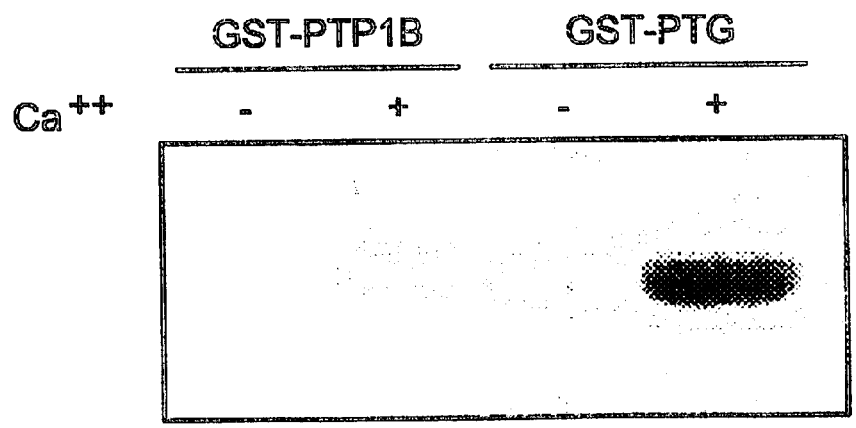

Phosphorylase kinase converts phosphorylase from the inactive b form to the active a form. This activation can be reversed via dephosphorylation by PP1C. Phosphorylase kinase can also be directly inactivated by PP 1. Because of the central role of phosphorylase kinase in regulating glycogen metabolism, it is also a candidate for association with PTG. GST-PTG-glutathione-Sepharose beads were incubated with 3T3-L1 adipocyte lysates, washed extensively, and assayed for phosphorylase kinase activity with [$^{32}$P]-γ-ATP and phosphorylase b as substrate. Calcium-stimulated phosphorylase kinase activity (Krebs E. G., et al, *Biochem.,* 1964;3:1022) was associated with GST-PTG, but not with GST-PTP1B (FIG. 4C). To confirm these results, the binding of phosphorylase kinase to PTG was also assayed using purified enzyme. As seen in FIG. 4D, the purified protein also specifically bound to the PTG-glutathione Sepharose beads. Interestingly, neither PP2A nor cAMP-dependent protein kinase in L1-adipocyte lysates bound to GST-PTG (data not shown), demonstrating the specificity of binding for both phosphatases and kinases to PTG. Taken together, these results imply that PTG can complex with each of the key proteins involved in regulating glycogen metabolism, although it is unclear whether all of the glycogen metabolizing enzymes are bound to a single PTG molecule, or if individual binding sites are shared between one or more proteins.

Overexpression of PTG increases insulin stimulated glycogen synthesis: The data presented above indicate that PTG can target to glycogen the two enzymes that are critical in controlling its metabolism, glycogen synthase, and phosphorylase a, as well as the major proteins that mediate the hormonal regulation of these enzymes, PP1C and phosphorylase kinase. These findings prompted us to examine whether overexpression of PTG could cause an increase in both basal and insulin-stimulated glycogen synthesis. CHO-IR cells express no detectable PTG transcript or protein (data not shown), and have a low basal rate of glycogen synthesis, which increases approximately 1.5- to 2-fold upon insulin treatment (FIG. 5). Overexpression of PTG in the CHO-IR cells caused a 7-fold increase in the basal rate of glycogen synthesis. Exposure of these cells to insulin produced another 2-fold increase, with total glycogen synthesis increased over 10-fold. It should be noted that only 20% efficiency of transfection was achieved in these experiments, suggesting that the 10-fold increase in maximal glycogen synthesis by PTG is significantly underestimated. These results demonstrate that PTG overexpression cannot only increase basal glycogen synthesis, but also dramatically elevate maximally insulin-stimulated glycogen accumulation in a poorly responsive cell line to a level comparable to that observed in insulin target cells (Lazar D. F., supra., 1995). However, because the sensitivity of these transfected cells to insulin remains unchanged, and because insulin does not appear to modulate PP1 C-PTG binding, PTG itself is not likely to be a direct target of insulin signaling.

DNA sequences, such as PTG cDNA can be subcloned into a variety of plasmid shuttle vectors, allowing rapid amplification and manipulation of recombinant DNA sequences in bacterial and mammalian hosts. Plasmid vectors used for routine manipulation of DNA, such as Bluescript SK (GenBank #X52328, Stratagene, La Jolla, Calif.), typically contain: 1) bacterial origin of replication, usually ColE1, 2)†Antibiotic resistance gene to select for transformed bacteria (usually Amp$^r$, for selection on Amplicillin), 3) Multicloning site containing unique restriction enzyme sites to facilitate insertion of desired DNA fragments. Plasmid vectors that are used to introduce desired DNA fragments into mammalian cells contain, in addition to those components required for bacterial vectors, a promoter sequence and a gene coding for resistance to eukaryotic antibiotics. The promoter region is typically a viral promoter (CMV, Simian Viras 40, SV40) that directs high expression of the cloned gene in mammalian cells, and the antibiotic resistance gene is typically Neomycin phosphotransferase (Neo$^r$), which confers resistance to the eukaryotic antibiotic neomycin. Viral (retrovirus and adenovirus) vectors typically contain all of the above mentioned components, in addition to viral sequences that allow recombinant DNA to be efficiently packaged into viral particles and infect the mammalian host cells. These types of viral vectors are widely used to introduce recombinant DNA into mammalian tissue culture cells and in gene therapy, where recombinant viral particles are used to infect tissues in vivo.

Many mammalian cell lines derived from a variety of tissues are used as model systems to examine intracellular processes in the laboratory. For example, the 3T3-L1 and 3T3-F442A cell lines, cloned from Swiss mouse embryo fibroblast 3T3 cultures (Green and Kehinde, 1974, *Cell* 1: 113–116), differentiate into adipocytes and are useful in studying adipogenesis and insulin action (Garcia de Herreros and Birnbaum, 1989, *J. Biol. Chem.*. 264:19994–19999). Other cell lines commonly used include NIH 3T3 fibroblasts (ATCC #CRL-1658), rat muscle cell line L6 (Proc. Natl. Acad. Sci. USA 61:477–483, 1968) and Chinese hamster ovary cells, CHO-K1 (ATCC #CRL-9618). Primary cells derived from isolated mammalian tissues can also be cultured in the laboratory, however these cells have a limited lifespan in culture and usually die after 7 to 10 days.

Recombinant DNA can be introduced (transfected) into mammalian cells either in culture or in vivo by a number of techniques. Calcium Phosphate-mediated transfection (Chen and Okayama 1987, *Mol. Cell. Biol.*, 7:2745–2752) is used with cells in tissue culture, however some cell types transfect at very low efficiency. Liposome-mediated transfection (Lipofectamine; Gibco-BRL) (Felgner, et. al., 1987, *Proc. Natl. Acad. Sci. USA* 84:7413–7417.) has been used to transfect cells resistant calcium phosphate mediated transfection. Virtually all cell types, including primary cells in vitro and in vivo, can be infected with recombinant retrovirus, making this method of DNA delivery particularly useful (Miller, et al., 1993, *Methods in Enzymology*, 217:581–599). Likewise, adenoviral-mediated gene transfer has been used to infect terminally differenciated cells and tissue (Becker et al. 1994, *Methods Cell Biol.*, 43:161–189), since adenoviral infection does not require actively dividing cells, as does retroviral gene transfer.

Human gene therapy has relied upon the ability of recombinant virus, both retrovirus and adenovirus, to deliver desired genes to the appropriate tissues in vivo. The expression of foreign genes using adenovirus vectors was first developed over a decade ago, and since then, adenovirus vectors have proven useful in studies of gene therapy and vaccine development, as well as in basic biology. In gene-therapy studies, effective gene transfer using adenovirus vectors has been demonstrated (Engelhardt, et al., 1994, *Proc. Natl. Acad. Sci. USA,* 91:6196–6200). Retroviral-mediated gene transfer has been successfully used to correct adenosine deaminase (ADA) deffiency in humans (Blaese, et al., 1995, *Science* 270:475–480; Kohn, et al., 1995, *Nature Med.*, 1:1017–1023).

The manufacture of animals having one or more endogenous genes deleted is well known to these skilled in the art. See, for example, U.S. Pat. Nos. 5,487,992 and 5,464,764, herein incorporated by reference, teach how to make animals having a gene deleted (also called a knock-out animal). in particular, U.S. Pat. Nos. 5,464,764 and 5,487,992 teach how to make knock-out mice.

Mice having a PTG knock-out are useful as animal models for increasing glycogen in cells, and are specifically useful as a model for diabetes.

The present invention is also usefuil in that new drugs can be identified by screening librarys of chemical compounds for agonists or antagonists (inhibitors) of the PTG protein.

The experimental presented below is intended to illustrate particular embodiments of the invention and is not intended to limit the specification, including the claims, in any manner.

EXPERIMENTAL

The examples and procedures set forth below are intended to illustrate particular embodiments of the invention and are not intended to limit the specification, including the claims, in any manner.

The following abbreviations are used herein:
A Adenosine
C Cytosine
G Guanosine
T Thymine
U Uracil
Ala Alanine
Arg Arginine
Asn Asparagine
Asp Aspartic Acid
Cys Cysteine
Glu Glutamic Acid
Gln Glutamine
Gly Glycine
His Histidine
Ile Isoleucine
Leu Leucine
Lys Lysine
Met Methionine
Phe Phenylalanine
Pro Proline
Ser Serine
Thr Threonine
Trp Tryptophan
Tyr Tyrosine
Val Valine
PTG Protein targeting to glycogen
CHO-IR Chinese hamster ovary cell expressing human insulin receptors
cAMP Cyclic adenosine monophosphate
kD Kilodaltons
DNA Deoxyribonucleic acid
cDNA Complimentary deoxyribonucleic acid
SDS-page Sodium dodecyl sulfate-polyacrylamide gel electrophonesis
GST Glutahione S-transferase
mRNA Messenger ribonucleic acid BSA Bovine serum albumin
KPBH Krebs-ringer phosphate-buffered saline
HEPES (N-[2-hydroxyethyl]piperazine-N'-[2-ethanesulfonic acid])
PNS Post nuclear supernatant
EDTA Ethylenediaminetetraacetic acid
CMV Cytomyalovirus
RNA Ribonucleic acid
MOPS 4-Morpholine propane sulfonic acid
PEG Polyethylene glycol
SSPE Standard saline phosphate EDTA
SDS Sodium dodecylsulfate
rRNA Ribosomal ribonucleic acid
EGTA Ethylene glycol-bis (β-aminoethylether)-N,N,N',N'-tetraacetic acid
ATP Adenosine triphosphate
UDP Uridine 5'-diphospho-α-D-glucopyranose
SD Standard deviation Cell Culture. Propagation and differentiation of 3T3-L1 fibroblasts has been described previously (Waters S. B., et al., Mol. Cell. Biol., 1995;15:2791). Chinese hamster ovary (CHO) cells expressing >1×10$^6$ human insulin receptors (IRs) were grown in alpha-minimal essential medium containing nucleotides, 100 U of penicillin/mL, 100 μg of streptomycin/mL, 10% fetal bovine serum, and 250 μg G418/mL. Cells were incubated at 37° C. in an 8% $CO_2$-air gas mixture. Prior to experiments involving insulin stimulation, CHO-IR cells were incubated in serum free medium for 3 hours, followed by the addition of 100 nmol insulin for an additional 15 minutes.

Construction of 3T3-L1 Adipocyte 2-Hybrid Library. 3T3-L1 Fibroblasts were differentiated to adipocytes, as described previously (Lazar D. V., et al., J. Biol. Chem., 1995;270:20801), and poly-(A$^+$) mRNA obtained via the Messenger RNA Isolation kit (Stratogene, La Jolla, Calif.). Five micrograms of poly-(A$^+$) mRNA was used to synthesize cDNA with the Stratogene cDNA synthesis kit. First strand synthesis utilized an oligo dT-XhoI primer, whereas the 5' end was ligated to an EcoRI adapter following second strand synthesis. cDNA Fragments were then ligated unidirectionally into EcoRI/XhoI digested pGAD-GH GAL4 activation domain plasmid (Clontech, Palo Alto, Calif.). Ligations were electroporated into E. coli D12S to yield >2×10$^6$ individual transformants.

2-Hybrid Screen. A Gal4p- DNA binding domain (BD) fusion of PP1C was constructed by cloning the entire PP1C open reading frame (a generous gift of A. Naim), contained within a 1.0 kb EcoRI/BamHI fragment, into the EcoRI/BamHI sites of pGBT9 (Clontech), creating BD-PP1C. Strain Y190 was transformed first with BD-PP1C, Trp+ prototrophs selected, and then transformed with 150 μg of 3T3-L1 adipocyte library DNA. Transformants were selected by plating cells on synthetic medium lacking tryptophan, leucine, and histidine (SD-Trp-Leu-His) and containing 25 mM 3-aminotriazole (ATZ). Yeast transformations were performed by the lithium acetate procedure of Geitz, et al., Nucleic Acids Res., 1992;20:1425. Colonies that appeared after 5 days of incubation at 30° C. were patched onto SD-Trp-Leu-His plates and then replica plated onto M63GV-Trp-Leu-His media containing 5-bromo-4-chloro-3-indolylphosphate-β-D-galacto pyranoside (X-gal; Gibco-BRL) for preliminary determination of β-galactosidase activity (Printen J. A. and Sprague G. F. Jr., Genetics, 1994;138:609). Of approximately 3.5×10$^5$ total transformants, 64 His$^+$ prototrophic colonies were recovered, of which 27 were β-galactosidase positive. Plasmids containing interacting cDNAs were rescued from strain Y190 by transforming into E. coli HB101 and plating onto M9 minimal media lacking leucine. HB101 contains a leuB deletion that can be complimented by the yeast LEU2 gene, thereby selecting for E. coli transformants carrying only the library plasmid. When individual Leu$^+$ HB101 transformants were analyzed, it was found that from a single plasmid rescue, 2 to 3 different plasmids were recovered, of which only a subset would be β-galactosidase positive upon retransformation into Y190 containing Gal4-PP1C. Apparently, individual yeast cells are able to take up more than one plasmid in the conditions used during the library transformation. This problem was circwnvented by growing the yeast preparations in SD-Trp-Leu-His+25 mM ATZ broth during plasmid rescue.

DNA Sequencing of PTG. Preliminary sequence information of all Gal4p-PP1 interacting cDNAs was obtained by double-stranded sequencing using an oligonucleotide complimentary to the 3' end of the GAL4-AD coding region of pGAD-GH. Sequencing was performed with an Appligen fluorescent dye terminator kit (Perkin-Elmer) and an ABI 8700 automated sequencer. The entire DNA sequence of clone B1-1 was obtained by subcloning a 1.0 kb EcoRI fragment of clone B1-1 into the EcoRI site of pCRII (Invitrogen) and sequencing both strands using both T7, SP6, and custom primers. Some sequencing was performed at the University of Michigan DNA sequencing core facility. DNA and protein sequence analysis was performed using BLAST and BESTFIT (Genetics Computer Group, Madison, Wis.).

GST-PTG Fusion Protein Production. In order to facilitate rapid purification of PTG protein for use in biochemical studies, a glutathione-S-transferase (GST) -PTG fusion was constructed. A 1.0 Kb EcoRI fragment from clone B1-1, encoding residues 8-293, was subcloned into the EcoRI site of pGEX-5X-3 expression vector (Pharmacia). Fusion protein was produced by IPTG induction of 1 L cultures of E. coli BL21(DE3)LysS and purified by affinity chromatography on glutathione-agarose beads.

Sub-Cellular Fractionation of PP1C Activity: Following a 3-hour serum deprivation in KRBH/0.5% BSA/2.5 mM glucose, L1 adipocyte cells were washed three times with ice cold PBS. Cells were scraped in homogenization buffer (50 mM HEPES, pH 7.2/2 mM EDTA/2 mg/mL glycogen/0.2% 2-ME/+ protease inhibitors). Samples were sonicated and centrifuged at 2500×g to remove nuclei and unlysed cells. The PNS was removed, and glycogen bound PTG was added. Samples were incubated at 4° C. for 60 minutes with gentle mixing. Lysates were subjected to centrifugation for 15 minutes at 10,000×g and 1 hour at 100,000×g to pellet plasma membranes and glycogen pellets, respectively. The final supernatant was called cytosol. The glycogen pellets were resuspended in homogenization buffer by 10 passes through a 23 gauge needle. Protein concentrations and PP1 activity were measured in the PNS, plasma membrane, glycogen pellet, and cytosolic fractions, as described previously (Lazar D. F., supra, 1995). Fractionation of pFPTG transfected CHO-IR cells into cytosol and glycogen pellet was performed similarly.

Transient Transfection Studies. To facilitate in vivo studies of PTG action, an expression vector containing an epitope tagged version of PTG was constructed. The FLAG-epitope (N-DYKDDDDK-C) (IBI) was introduced into pCl-neo (Promega) by ligating complementary oligonucleotides into NheI/EcoRI digested vector. A 1.0 EcoRI fragment from clone B1-1 was cloned in-frame at the EcoRI site of the resulting plasmid, producing plasmid pFPTG. The FLAG-PTG fusion is expressed from the strong CMV enhancer/ promoter. CHO cells expressing insulin receptor (CHO-IR) were transfected with Lipofectamine (Gibco-BRL) according to manufacturer recommendations. Typically, 1 μg of pFPTG/6 μL Lipofectamine was used per 60 mm dish to achieve 20% to 30% transfection efficiency, as determined by a CMV-lacZ reporter vector transfected in parallel.

Immunoprecipitation and Immunoblotting. CHO-IR cells transfected with pFPTG were sonicated in homogenization buffer and subjected to 14000×g centrifugation for 10 minutes at 4° C. to remove nuclei and cell debris. FLAG-PTG was immunoprecipitated from the supernatant by incubation with 10 μg of αFLAG antibody (IBI) for 1 hour at 4° C. Immune complexes were precipitated by incubation with Protein A/G-agarose for 1 hour at 4° C. and washed four times with homogenization buffer prior to the addition of SDS-sample buffer. Immunoprecipitates and subcellular fractions were separated on SDS-polyacrylamide gels and transferred to nitrocellulose. Immunoblots were performed with either FLAG monoclonal antibody or with PP1C polyclonal antibody (a generous gift from Dr. J. Lawrence). The primary monoclonal and polyclonal antibodies were detected with horseradish peroxidase-conjugated anti-mouse or anti-chicken IgG, respectively, and visualized by the enhanced chemiluminescence detection system (Amersham).

Northern Blot Analysis: Total RNA was isolated from 3T3-L1 fibroblast cells and fully differentiated 3T3-L1 adipocyte cells by the acid guanidinium thiocyanate-phenol-chloroform extraction method (Rnasol; Biotex Laboratories). RNA samples (15 μg) were electrophoresed in 1.2% agarose/2.2 M formaldehyde/1×MOPS and transferred to nylon membrane (Hybond; Amersham) by capillary difflusion. The transfer membrane was pre-hybridized for 1 hour in FBY hybridization buffer (10% PEG/1.5× SSPE/7% SDS) and hybridized overnight at 65° C. with the 1.0 kb EcoRI fragment of clone B1-1, which was gel purified and labeled with [α-$^{32}$P]dCTP by random priming (sp act. >1×10$^9$ cpm/μg DNA). Following hybridization, the blot was washed at 65° C. in 2×SSC/0.1% SDS for 15 minutes, then washed twice in 0.1×SSC/0.1% SDS at 65° C. for 15 minutes each time. Equal loading of RNA was determined by ethidium bromide staining of rRNA and by probing for β-actin, as described above.

Glycogen Synthase and Glycogen Synthesis Assays. Glycogen synthase activity associated with immobilized GST-PTG was determined as described previously (Lazar D. F., supra., 1995). Briefly, 100 μL of GST-PTG bound to glutathione-agarose beads was resuspended in 725 μL of glycogen synthase buffer (50 mM HEPES, pH 7.8/100 mM NaF/10 mM EDTA) plus 25 μL (0.1 U) purified glycogen synthase (Sigma), followed by incubation at 4° C. for 1 hour with gentle mixing. The agarose beads were washed four times with glycogen synthase buffer., brought to a final volume of 300 μL and 50 μL assayed for glycogen synthase activity by measuring the incorporation of UDP-[$^{14}$C] glucose into glycogen, both in the presence and absence of 10 mM glucose-6-phosphate (Sigma). The accumulation of glycogen in intact pFPTG transfected CHO-IR cells was determined by an adaptation of the method of Lawrence J. C., et al., *J. Biol. Chem.*, 1977;252:444 as described previously (Lazar D. F., supra., 1995).

In Vitro Binding Assays. Phosphorylase kinase: 50 μL of GST-PTG fusion protein beads was added to 750 μL homogenization buffer containing 0.15 M NaCl, 0.1% BSA, and 25 μg of [$^{32}$P]-labeled phosphorylase a. The tubes were incubated at 37° C. for 20 minutes, washed four times with homogenization buffer, and proteins separated by SDS-PAGE, followed by autoradiography (Lawrence J. C., supra., 1977). One hundred microliters of GST-PTG bound to glutathione-agarose beads was resuspended in 725 μL of glycogen synthase buffer (50 mM HEPES, pH 7.8/100 mM NaF/10 mM EDTA) plus 25 μg (0.1 U) purified glycogen synthase (Sigma), followed by incubation at 4° C. for 1 hour with gentle mixing. The agarose beads were washed four times with glycogen synthase buffer, brought to a final volume of 300 μL and 50 μL assayed for glycogen synthase activity (Lazar D. F., supra, 1995) by measuring the incorporation of UDP-[$^{14}$C]glucose into glycogen, both in the presence and absence of 10 mM glucose-6-phosphate (Sigma).

Phosphorylase Kinase: Fifty microliters of fusion protein beads were incubated with 10 μg purified phosphorylase kinase (Gibco) in homogenization buffer plus 0.15 M NaCl and 0.1% BSA, or with 3T3-L1 adipocyte cell lysate, incubated 30 minutes at 4° C. and washed four times with the same buffer. Ten microliter beads were assayed (Lazar D. F., supra., 1995) in 50 mM HEPES, pH 7.4, 10 mM MgCl, 1 μM okadaic acid, in the absence (1 mM EGTA) or presence (0.5 mM) of Ca$^{++}$. Two micrograms phosphorylase b, 20 μM cold ATP, and 2 μCi [$^{32}$P]-g-ATP per tube was added and allowed to incubate at 37° C. for 5 minutes. At the end of the incubation period, SDS-sample buffer was added and the proteins separated by SDS-PAGE on a 10% gel.

Isolation of Human and Mouse Genomic PTG Sequence. Murine and human genomic PTG sequences were obtained by screening the respective genomic Bacterial Artificial Chromosome (BAC) (Shizuya H, et al., *Proc. Natl. Acad. Sci., USA*, 1992;89:8794; Kim U-J, et al., *Genomics*, 1996;34:213) library by hybridization to a [$^{32}$P]-labeled 1.0 kb cDNA fragment from clone B2-2. Hybridization of probe DNA to filters spotted with BAC DNA library was performed by Research Genetics, Huntsville, Ala. The source of the mouse genomic DNA is the cell line, CJ7 (Swiatek P. J. and Gridley T., *Gene and Dev.*, 1993;7:2071), derived from mouse strain 129SV. The sources of human DNA are the cell line 978SK and human sperm. Screening of the human BAC library resulted in the identification of three hybridization positive BAC clones (103 D21, 117C9, 255E4) and four positive clones from the mouse BAC library (201 D24, 211 P10, 219K2, 427F20). Human genomic BAC clone 255E4 and mouse genomic BAC clone 201D24 were chosen for further characterization following southern analysis with the labeled 1.0 kb cDNA fragment from clone B2-2 to confirm the presence of hybridizing DNA sequences.

Characterization of Human Genomic PTG DNA Sequences. To identify DNA frgents containing the PTG coding region, human BAC clone 255E4 (5 μg) was digested with EcoRI (1 unit) at 37° C. for 1 hour prior to separation of the resulting DNA fragments by electrophoresis through a 0.6% agarose gel. DNA fragments were transferred to nylon membrane (Hybond, Amersham) by capillary diffusion and probed with cDNA fragment encompassing the PTG coding sequence from clone B2-2. The transfer membrane was pre-hybridized for 1 hour in FBY hybridization buffer (10% PEG/1.5×SSPE/7% SDS) and hybridized overnight at 65° C. with the 1.0 kb EcoRI fragment of clone B1-1, which was gel purified and labeled with [α-$^{32}$P]dCTP by random priming (sp act. >1×10$^9$ cpm/mg DNA). Following hybridization, the blot was washed at 65° C. in 2×SSC/0.1% SDS for 15 minutes, then washed twice in 0.1×SSC/0.1% SDS at 65° C. for 15 minutes each time. A 5.0 kb EcoRI fragment was found to hybridize to the B1-1 PTG probe and was subsequently cloned into the EcoRI site of vector pBluescript II SK$^-$ (Stratogene, La Jolla, Calif.), creating the plasmid pJPD23. Preliminary sequence analysis of subcloned 5.0 kb fragment was performed by using T3 and T7 primers complementary to vector sequences flanking the inserted fragment. Complete sequence information was obtained by synthesizing oligonucleotide primers complementary to both positive and negative strands of the inserted human genomic DNA. Sequencing was performed at The University of Michigan DNA sequencing core facility with an Appligen fluorescent dye terminator kit (Perkin-Elmer) and an ABI8700 automated sequencer. Assignment of the human PTG open reading frame continued within the 5.0 kb genomic sequence is based upon sequence comparison with the mouse PTG cDNA from the 2-hybrid clone B2-2 and upon favorable translational initiation sequences surrounding the putative initiating methionine (Kozak M, *J. Cell Biol.*, 1989;108:229).

Characterization of Mouse Genomic PTG DNA Sequences. The mouse BAC clone 201D24 was subjected to southern analysis, as described for the human genomic BAC clone, except BamHI (1 unit, 37° C., 2 hours) was used to digest 5 µg of DNA. A 7.0 kb hybridizing fragment was identified and subcloned into the BamHI site of pBluescript II Sk⁻, creating pJPD27. An overlapping 5.0 kb EcoRI fragment 3' to the PTG open reading frame was identified by restriction digest of BAC clone 201D24 (5 µg) with EcoRI (1 unit, 37° C., 2 hours), followed by southern analysis using a 0.8 kb SstI-BamHI fragment from the extreme 3' of genomic DNNA of pJPD27. This fragment was isolated from the agarose gel and ligated into the EcoRI site of pBluescript II Sk⁻, creating plasmid p201-3'. Sequence information of the additional 2.0 kb genomic DNA 3' to the BamHI site of pJPD27 was obtained as described above for the human genomic PTG sequence.

Construction of PTG Knockout Vector. To further characterize the physiological role of PTG in overall glycogen metabolism in vivo, a targeted replacement vector was constructed to delete the PTG coding sequences from a mouse genome. pKO Scrambler V901 vector (Lexicon Genetics, Inc, The Woodlands, Tex.) forms the backbone of the targeting vector, as this vector has scrambled polylinkers, for insertion of 5' and 3' homologous genomic DNA, flanking a unique restriction site for insertion of a positive selectable marker (neoʳ for selection of transfected ES cells on the antibiotic G418). pKO Scrambler V901 also contains a unique restriction site for the insertion of a negative selection element (Thymidine Kinase) for positive-negative selection strategies, which has been reported to increase targeting efficiency to the desired locus 2- to 20-fold (Hasty P. and Bradley A. in *Gene Targeting: A Practical Approach*, 1993, A. L. Joyner, Ed., IRL Press, Oxford). A positive selection cassette containing the Neomycin Phosphotransferase gene under the control of the PGK promoter was excised from plasmid pKO selectNEO V800 (Lexicon Genetics, Inc, The Woodlands, Tex.) by digestion with the restriction enzyme AscII (New England Biolabs, Beverly, Mass.) and subcloned into the unique AscII site ofpKO Scrambler V901, creating plasmid pKO-neo. A negative selection cassette containing the thymidine kinase gene under the control of the MC1 promoter was subcloned into the unique RsrII site of pKO-neo by digestion of plasmid pKO SelectTK V800 (Lexicon Genetics, Inc, The Woodlands, Tex.) with RsrII (New England Biolabs, Beverly, Mass.) followed by separation and isolation of the appropriate restriction fragment (2.0 kb) by electrophoresis through a 1.0% agarose gel, creating plasmid pKO-TK/neo. A 2.0 kb region of DNA 5' to the PTG coding region was amplified by Polymerase Chain Reaction (PCR) using primers 5'-CGA<u>GGATCC</u>TTGTCTTCTCTGCAGATG-3' (SEQ ID NO.: 7) and 5'-GCT<u>GGTACC</u>TGAATGAGCCAAGCAAATCCTC-3' (SEQ ID NO.: 8), which contain BamHI and KpnI sites, respectively. The amplified DNA product was then cloned into the BglII-KpnI of plasmid pKO-TK/neo, creating the plasmid pKO-TK/neo-5'. The 3.5 kb 3' homology region of genomic PTG DNA was cloned into the EcoRI-SalI sites of pKO-TK/neo-5' by first digesting pJPD27 (1 µg) with SmaI (1 unit, 22° C., 2 bours), and inserting a SalI oligonucleotide linker (5'-CCG<u>GTCGAC</u>CGG-3') (SEQ ID NO.: 9), creating plasmid pJPD27ΔSma. The 3.5 kb EcoRI-SalI fragment from pJPD27ΔSma was then ligated into the EcoRI-SalI sites of pKO-TK/Neo-5' to create the targeting vector pKO-PTG.

A 0.5 kb 5' DNA probe was generated by PCR amplification from plasmid pJPD27 with the T3 specific primer, complementary to DNA sequences contained within the vector pBluescript II Sk⁻ and a primer specific to the extreme 5' region of mouse genomic DNA sequence (5'-GCAGAGAAGACAAAACCAC-3') (SEQ ID NO.: 10). The 3' DNA probe was generated by digestion of plasmid p201-3' with BamHI and isolation of the resulting 0.8 kb fragment following electrophoretic separation on a 1.5% agarose gel.

DETAILED DESCRIPTION OF THE FIGURES

FIG. 1. Sequence comparison of PTG with glycogen localizing subunits of PP1C. BESTFIT sequence comparison program was used to align and compare the primary amino acid sequences of PTG, $G_L$, RG1 and Gac 1. The boxed regions represent areas of similarity and the sites of conservation are indicated by shading.

FIG. 2. PP1C binding and glycogen localizing activity of PTG protein.

(A) PP1C binds PTG in vivo. pCI-neo expressing FLAG-PTG from the CMV promoter was transiently transfected into CHO-IR cells and immunoprecipitated from cell lysates with antibodies directed against the FLAG epitope. Precipitates were analyzed by SDS-PAGE on a 4% to 20% gel, transferred to nitrocellulose and blotted with αPP1C polyclonal antibodies. Immunoreactive proteins were visualized by Enhanced Chemiluninescence (ECL).

(B) PTG partitions to the glycogen pellet. Lysates from pFLAG-PTG transfected or untransfected CHO-IR cells were fractionated by centrifugation into 14K ×g supernatant (14,000×g, 15 min, supernatant), cytosol (100,000×g, 1 hr, supernatant) or glycogen pellet (100,000×g, 1 hr, pellet), and proteins were subjected to SDS-PAGE and immunoblotted with αFLAG antibodies.

(C) PTG overexpression causes translocation of PP1C to the glycogen pellet. Lysates from pFLAG-PTG transfected or untransfected CHO-IR cells were fractionated by centrifugation and immunoblotted as in (A) to determine relative levels of PP1 C contained in the various fractions. All fractions were normalized for protein concentration prior to loading.

(D) PTG targets PP1C to glycogen in vitro. PTG dependent localization of PP1C to the glycogen pellet was determined by incubated 3T3-L1 adipocyte cell lysates with bacterially expressed GST-PTP1B or GST-PTG prior to subcellular fractionation as above. PP1C activity in the glycogen pellet was measured as described previously (Lazar D. F., supra., 1995).

FIG. 3. Tissue distribution of PTG expression.

(A) PTG is expressed in insulin responsive tissues. A multi-tissue northern blot (Clonetech) was hybridized overnight at 65° C. with a 1.0 kb EcoRI fragment of clone B1-1, which was labeled with [α-$^{32}$P]dCTP by random priming, and exposed to film for 24 hours.

(B) PTG expression is induced by adipocyte differentiation. 3T3-L1 fibroblast and fully differentiated 3T3-L1 adipocyte total RNA was isolated and electrophoresed (15 μg) in 1.2% agarose/2.2 M formaldehyde/1×MOPS, followed by transfer to nylon membrane by capillary diffusion. The transfer membrane was hybridized and probed as in (A). Equal loading of RNA was determined by ethidium bromide staining of rRNA and by probing for β-actin transcript. Molecular size markers (kb) are indicated on the left.

FIG. 4. Binding of phosphorylase a, glycogen synthase, and phosphorylase kinase to PTG.

(A) PTG binds to phosphorylase a [$^{32}$P]-labeled phosphorylase a (25 μg) was incubated with the indicated fusion protein immobilized to glutathione-agarose beads for 1 hour at 4° C. in homogenization buffer (50 mM HEPES, pH 7.2/2 mM EDTA/2 mg/mL glycogen/0.2% 2-ME/0.1 mM PMSF/1 mM benzamidine/10 μg/mL aprotinin), followed by washing four times with homogenization buffer prior to the addition of SDS sample buffer. Proteins were separated by SDS-PAGE and the gel exposed to film.

(B) PTG binds glycogen synthase. One hundred microliters of GST-PTG bound to glutathione-agarose beads was resuspended in 725 μL of glycogen synthase buffer (50 mM HEPES, pH 7.8/100 mM NaF/10 mM EDTA) plus 25 μL purified glycogen synthase (Sigma), followed by incubation at 4° C. for 1 hour with gentle mixing. The agarose beads were washed four times with glycogen synthase buffer and assayed for glycogen synthase activity.

(C, D) Phosphorylase kinase binds to PTG. Fifty microliters of bacterially expressed GST-PTG bound to glutathione-agarose beads was incubated with of 3T3-L1 adipocyte cell lysate (C) or 10 μg purified phosphorylase kinase (Gibco) (D) in homogenization buffer. Samples were incubated 30 minutes at 4° C. and washed four times with the same buffer. Ten microliter beads were assayed for phosphorylase kinase activity using 2 μg phosphorylase b per sample in the absence (1 mM EGTA) or presence (0.5 mM) of Ca$^{++}$. Complexed proteins were separated on a 10% SDS-polyacrylamide gel and radiolabeled phosphorylase a was visualized by autoradiograpby.

FIG. 5. Glycogen synthesis in CHO-IR cells overexpressing PTG. CHO-IR cells were grown to 40% to 50% confluency in 6-well dishes and transiently transfected with pFLAG-PTG. Forty-eight hours after transfection, cells were serum deprived for 3 hours and glycogen accumulation in intact pFLAG-PTG or lacZ transfected cells, in the presence or absence of 100 nM insulin, was determined. Results are expressed as means of triplicate determinations, of SD, and were repeated in two separate experiments.

What is claimed is:

1. An isolated murine protein comprising the amino acid sequence SEQ. ID. NO: 2.

2. An isolated human protein comprising the amino acid sequence SEQ. ID. NO: 4.

3. An isolated murine genomic DNA molecule comprising the nucleic acid sequence SEQ. ID. NO: 1.

4. An expression vector that contains a murine genomic DNA molecule comprising the sequence of claim 3.

5. A isolated host cell containing an introduced murine genomic DNA molecule comprising the sequence of claim 3.

6. An isolated human genomic DNA molecule comprising the nucleic acid sequence SEQ. ID. NO: 3.

7. An expression vector that contains a human genomic DNA molecule comprising the sequence of claim 6.

8. A isolated host cell containing an introduced human genomic DNA molecule comprising the sequence of claim 6.

9. An isolated murine cDNA molecule comprising the nucleic acid sequence SEQ. ID. NO: 5.

10. An expression vector that contains a murine cDNA molecule comprising the sequence of claim 9.

11. A isolated host cell containing an introduced murine cDNA molecule comprising the sequence of claim 9.

12. An isolated human cDNA molecule comprising the nucleic acid sequence SEQ. ID. NO: 6.

13. An expression vector that contains a human cDNA molecule comprising the sequence of claim 12.

14. A isolated host cell containing an introduced human cDNA molecule comprising the sequence of claim 12.

* * * * *